(12) United States Patent
Liu-Chen et al.

(10) Patent No.: US 6,416,987 B1
(45) Date of Patent: Jul. 9, 2002

(54) MUTANTS OF THYMIDYLATE SYNTHASE AND USES THEREOF

(75) Inventors: Xinyue Liu-Chen, New York, NY (US); Youzhi Tong, Union, NJ (US); Joseph R. Bertino, Branford, CT (US); Debabrata Banerjee, Bellerose, NY (US)

(73) Assignee: Sloan Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/367,007

(22) PCT Filed: Feb. 3, 1998

(86) PCT No.: PCT/US98/02145

§ 371 (c)(1),
(2), (4) Date: Oct. 15, 1999

(87) PCT Pub. No.: WO98/33518

PCT Pub. Date: Aug. 6, 1998

Related U.S. Application Data

(60) Provisional application No. 60/037,163, filed on Feb. 4, 1997.

(51) Int. Cl.[7] .............................. C12N 9/12; C12N 15/54
(52) U.S. Cl. ................. 435/193; 435/252.3; 435/320.1; 435/325; 536/23.2
(58) Field of Search .............................. 435/193, 320.1, 435/325, 252.3, 372; 536/23.2; 424/94.5, 94.3

(56) References Cited

PUBLICATIONS

Santi D.V., Mutagenesis, structure and function studies of thymidylate synthase. Nucleic Acids Symposium Series. 1993, vol. 29, pp. 103–105.*

Schiffer et al, Crystal structure of human thymidylate synthase: A Structural Mechanism for Guiding Substrate into the Active Site, Biochemistry, 1995, 34, 16279–16287.*

Barbour K. V. et al, Single Amino Acid Substitution Defines a Naturally Occuring Genetic Variants of Human Thymidylate Synthase, Mol. Pharmacol., 1990, 37, 515–518.*

Schimmel P., Functional Analysis Suggests Unexpected Role for Conserved Active–Site Residue in Enzyme of Known Structure, Proc. Natl. Acad. Scis. USA, 1993, 90, 9235–9236.*

* cited by examiner

*Primary Examiner*—Rebecca E. Prouty
*Assistant Examiner*—Malgorzata A Walicka
(74) *Attorney, Agent, or Firm*—Benjamin Aaron Adler

(57) ABSTRACT

The present invention provides a mutated human TS, said mutated synthase differing from wild type TS at amino acid residue 49, amino acid residue 52, amino acid residue 108, amino acid residue 221 or amino acid residue 225. Also provided is cDNA mutated human TSs and novel vectors and host cells and methods of using the mutated human TSs.

11 Claims, 9 Drawing Sheets

MUTANTS OF THYMIDYLATE SYNTHASE AND USES THEREOF

This is US national stage application of international application PCT/US98/02145 filed Feb. 3, 1998, which claims benefit of priority under 35 USC 119(e) of provisional U.S. application Ser. No. 60/037,163, filed Feb. 4, 1997, now abandoned.

BACKGROUND OF THE INVENTION

1. Field of the Invention

The present invention relates generally to the fields of gene therapy and biochemical pharmacology. More specifically, the present invention relates to mutants of human enzyme thymidylate synthase and uses thereof.

2. Description of the Related Art

Thymidylate synthase (TS, EC 2.1.1.45) catalyzes the rate limiting step in the sole de novo biosynthesis pathway to thymidylate, which is necessary for DNA synthesis and repair (Carreras et al., 1995). The mechanism of TS activity involves the reductive methylation of the substrate, 2'-deoxyuridine 5'-monophosphate (dUMP) by transfer of a methylene group from the cofactor, 5,10-methylenetetrahydrofolate ($CH_2H_4$folate), to generate 2'-deoxythymidine 5'-monophosphate (dTMP) and 7,8-dihydrofolate ($H_2$folate). The inhibition of the TS pathway results in a thymineless state, which is toxic to rapidly dividing cells which have a high dTTP demand for DNA synthesis. This cytotoxicity is caused by DNA fragmentation and misincorporation of dUTP due to dTTP depletion. If there is enough supplied exogenous thymidine, cells survive through the salvage pathway depending on the use of thymidine kinase (TK). However, in normal tissues and in some tumor cells, the concentrations of circulating thymidine may not be sufficient to keep cells normally growing (Touroutoglou et al., 1996).

As a consequence, TS is an attractive target for anti-cancer drug design due to its crucial role in maintaining pools of thymidylate for DNA synthesis. Since the 1950s, many analogues of both the pyrimidine substrate (dUMP) and folate cofactor ($CH_2H_4$folate) have been synthesized and tested as potential anti-cancer therapeutics. However, although a number of inhibitors that tightly bind to TS were discovered, before 1995, 5-fluorouracil (5-FU) was the sole TS-targeted drug approved for clinical application. In vivo, 5-FU is metabolized to 5-fluoro-2-deoxyuridylate (FdUMP) that subsequently occupies the dUMP binding site forming a ternary complex with the enzyme and the folate cofactor, resulting in inhibition of TS. As the three-dimensional structures of TS have been revealed, the folate binding site in TS has been explored for the design of highly specific inhibitors (Jackman et al., 1995b), and have led to the emergence of novel folate analogues, such as tomudex (ZD1694), BW1843U89, AG331 and AG337 etc. These agents as the new generation TS-directed inhibitors have entered clinical trail in recent years. The approval of tomudex for treatment of advanced colorectal cancer in the United Kingdom occurred last year.

The major blood folate is 5-methyl-tetrahydrofolate (5-$CH_3$—$H_4$folate), which enters cells via membrane transports [or called reduced folate carriers (RFC)]. Once inside the cell, 5-$CH_3$—$H_4$folate is metabolized by methionine synthase to tetrahydrofolate. This coenzyme is converted by serine hydroxymethyltransferase to 5,10-methylene-tetrahydrofolate and also polyglutamated by folylpolyglutamate synthase (FPGS) to become 5,10-methylene-tetrahydrofolate polyglutamates [$CH_2H_4$folate$(Glu)_n$]. $CH_2H_4$folate$(Glu)_n$, as a cofactor, donates its one-carbon unit and two electrons to the reductive methylation reaction converting dUMP to dTMP. Dihydrofolate ($H_2$folate) is a product of this process, which requires the sequential action of dihydrofolate reductase (DHFR) and serine hydroxymethyltransferase in order to resynthesize $CH_2H_4$folate$(Glu)_n$. Inhibition of DHFR by methotrexate (MTX) may lead to an accumulation of folates in the inactive $H_2$folate form, resulting in depletion of $CH_2H_4$folate and dTMP.

There is much interest in correlating enzyme structure and function using mutagenesis. To date, several hundred mutations have been made in L. casei, E. coli and human TS (Climie et al., 1990b; Michael et al., 1990). Most of mutations in L. casei were produced by cassette mutagenesis (Wells et al., 1985; Climie et al., 1990a). The synthetic L. casei TS gene was engineered by creating over 30 unique restriction sites about equally spaced throughout the entire gene, providing "replacements sets" in which several target amino acids were replaced by a large number of substitutions. Another approach involving the introduction of an amber stop codon were adopted to generate multiple mutants of E. coli TS (Michaels et al., 1990; Kim et al., 1992). Using these approaches the various mutants in either L. casei or E. coli system were first screened for catalytic activity of TS by genetic complementation in a TS-deficient E. coli host, and then mutants of interest characterized by kinetic studies. A few mutants of human TS and their expressed enzymes in mammalian cells have also been studied. The mutant human TSs were also tested to complementation of the growth of TS-negative E. coli stains in the absence of thymine to determine if the activity of an altered enzyme is sufficient to support growth. However, the correlation of a mutant human TS and drug resistance can not be interpreted by this complementation study in a bacterial system and mammalian cells lacking TS are required. The three-dimensional structure of human TS has provided the impetus to generate mutants of human TS having novel enzyme properties such as drug resistance.

Prediction of properties of enzymes obtained by site-directed mutations is poor. When the enzyme accommodates a single amino acid substitution, readjustment of neighboring residues may occur, resulting in structural plasticity. TS is one of best examples for observing this phenomenon. In general, TS can tolerate amino acid substitutions even in a highly conserved residue that is important for enzyme structure or function. In a few cases, a single amino acid replacement causing dramatic change in properties of TS was also found. By reviewing the mutations already made, it was found that highly conserved residues are hot spots for amino acid substitutions (Carreras et al., 1995), and there are a few residues such as Arg50, Glu87, Trp109, Cys195, Arg215, Asp218, and Tyr258 especially sensitive to substitution (Stroud et al., 1993). All of these residues are in the substrate or folate binding site.

Cys195 (ec146, lc198) involved in the binding of 2'-deoxyuridylate as well as initiating the catalytic process could only be modified to Ser for E. coli TS and still retain activity, albeit severely diminished activity. None of the comparable L. casei mutants showed detectable activity (Dev et al., 1988; Climie et al., 1990b). Conserved Arg residues at positions 50, 215, 175, and 176 form a positively charged binding surface for the phosphate anion of dUMP. In L. casei, For Arg175, another completely conserved residue could be replaced by a neutral (Ala, Thr), positive (Lys). or negative (Glu) amino acid without drastic changes in substrate binding or catalytic activity (Santi et al, 1990).

Most substitutions for Arg176 of either *E. coli* or *L. casei* TS result in little impairment of function. In contrast, Arg218 could not resist any amino acid shifts.

The Arg50 loop, having less than 1.0 Å movement and reorientation upon Arg50 (ec21, lc23) binding to the phosphate of dUMP, is a highly conserved region. For Arg50, only four amino acids (Gly, Pro, Ser, and His) in *E. coli* TS and three residues (Val, Ile, and Gln) in *L. casei* TS are substitutable with retention of 10–50% of the wild-type activity (Zhang et al., 1990; Michaels et al., 1990). Asp49 (ec20, lc22) is quite sensitive to mutagenesis, except for replacements by the two polar (Cys, Ser) and one acidic (Glu) residues, all *E. coli* Asp49 mutants do not complement growth of TS-negative cells. In *E. coli* TS, Thr51 (ec22, lc24) tolerates substitutions of Pro, Ser, Tyr, Gln and Lys. Surprisingly, contrary to those neighbor residues, Gly52 (ec23, lc: His52) accepts any mutations. This residue has apparent reorientation upon the formation of ternary TS complex (Kim et al., 1992).

Trp109 (ec80, lc82) and Asn112 (ec: Trp83, lc: Trp85) are highly conserved residues that form hydrophobic contacts with both dUMP and $CH_2H_4$folate. Trp109 activity could not be fully restored by any of the substitutions except phenylalanine for *E. coli* TS, but showed high activity by three amino acid (Phe, Tyr and His) changes for *L. casei* TS (Michaels et al., 1990). Asn112 was only mutated to Phe for *L. casei* TS and the altered enzyme remained functional, but the W109F/N112F double mutant of *L. casei* was inactive (Carreras et al., 1995). Phe59 (ec30, lc32) forms part of the substrate binding pocket in tertiary structure. Leu and Tyr replacements for Phe59 of *E. coli* TS yield enzymes that complement the TS-deficient *E. coli* strain, but TS activity was totally lost for other substitutions (Kim et al., 1992).

The C-terminus region of TS plays a critical role in folate binding and catalysis (Perry et al., 1993). Deletion of just the residue Val313 results in TS protein that can bind both ligands but is catalytically inactive because the protein is incapable of closure to sequester the reactants. However, Val313 could tolerate almost all substitutions and many mutants were as active as wild-type TS (Climie et al., 1992; Carreras et al., 1992). A few mutagenesis studies for human TS have been published. Gln214, being believed in a kink region for three (β-sheet formation of the central core of the polypeptide, is highly conserved in all TSs. Cell growth of the TS-negative *E. coli* was supported by Glu, His, Lys, or Ala, but not by Ser, Cys, or Trp substitutions (Zhao et al., 1995).

Until recently, only one mutation in TS has been reported to be related to TS-directed drug resistance. Tyr33 of human TS is one of 40 amino acid residues that are invariant among all reported TS sequences. The Tyr33 to His33 substitution was discovered in a human colon tumor cell line and conferred approximately a 3- to 4-fold resistance to FdUMP, a metabolite of the chemotherapeutic prodrug 5-fluorouracil. This mutation affects the catalytic properties of the TS enzyme, showing an 8-fold drop in $k_{cat}$ for the reaction. The $K_m$ values for both dUMP and $CH_2H_4$folate were not significantly different between the mutant and wild-type TS.

The crystal structure of human TS has shown that the side chain of Tyr is not directly involved in ligand binding site of the human TS. However, the hydroxyl oxygen of Tyr33 is hydrogen bonded to the backbone carbonyl oxygen of residue 219 at the first turn of the central hydrophobic helix J (residues 219–242). The first turn of helix J is consisted of eight amino acid residues (219–226), five of which are highly conserved and two (Leu221 and Phe225) form a hydrophobic pocket for the PABA ring of the cofactor. The drug-resistant mutation can be interpreted in terms of induced change by reorientation in the initial turn of the helix J to be no longer optimal for ligand binding. Why some substitutions are active in *E. coli* but not in *L. casei* TS, and vice versa is not known.

The discovery and development of TS inhibitors was based on molecular structures and properties of TS and its pyrimidine substrate or folate cofactor, especially as the three-dimensional structures of several unliganded and liganded TSs at the atom level of resolution were achieved. The first compounds to have clinically significant TS-inhibiting activity were the fluoropyrimidines 5-FU and FdUrd, which are metabolized to 5-fluorodeoxyuridine monophosphate (FdUMP) that subsequently occupies the substrate binding site leading to a stable and inactive TS complex. In addition, they also may be incorporated into RNA or DNA via fluoro-UTP or 5-fluoro-dUTP, respectively. Therefore, fluoropyrimidines are not pure TS inhibitors and are susceptible to metabolic degradation in vivo. In contrast, folate analogues may be designed as more specific and more stable TS-specific inhibitors. Moreover, the cofactor $CH_2H_4$folate is a relatively large molecule, which provides a variety of sites, amenable to manipulation in drug design (Schoichet et al., 1993).

ZD1694 and BW1843U89 are new, promising antifolates that are derived from the CB3717 chemical scaffold, which are characterized as classical antifolate TS inhibitors. They contain a glutamate moiety and can be metabolized to noneffluxable polyglutamate forms within the cell. The polyglutamylated TS inhibitors bind tighter than the corresponding monoglutamylated forms. By comparison, the nonclassical antifolate TS inhibitors. such as AG337 and AG331, lacking the glutamate, have recently been developed.

The antineoplastic agent 5-FU is a mechanism-based inhibitor of TS, which is metabolized to FdUMP that forms a stable covalent adduct with $CH_2H_4$folate as a steady-state intermediate, resulting in inhibition of TS. CB3717 ($N^{10}$-propargyl-5, 8-dideazafolic acid), a lead compound as analogue of $CH_2H_4$folate, is a 2-amino-4-hydroxy quinazoline carrying a propargyl group on N-10 that greatly increases the affinity of TS, with $K_i$ of 2.7 nM. CB3717 demonstrated antineoplastic activity in Phase I trials, but its development was abandoned due to unpredictable severe renal and hepatic toxicity caused by its poor aqueous solubility. Tomudex (N-(5-[N-(3,4-dihydro-2-methyl-4-oxoquinazolin-6-ylmethyl)-N-methyl amino-]-2-thenoyl)-L-glutamic acid) was developed based on the molecular structure of CB3717. This quinazoline folate analogue, designed to be more water-soluble than CB3717 to avoid some side-effects such as nephrotoxicity, is a highly selective inhibitor of mammalian TS (Jodrell et al., 1991). Similar to CB3717, tomudex results in decreased TMP production, which leads to inhibition of DNA synthesis, resulting in cell death (Jackman et al., 1991a, b, & c).

Tomudex is a mixed noncompetitive TS inhibitor. In contrast to CB3717, tomudex enters cells using the reduced folate carrier (RFC). In the cell it is an excellent substrate for FPGS with an affinity 30 times higher than that of CB3717, and it is rapidly polyglutamylated by FPGS. The polyglutamated forms (n=2–6) are up to 100-fold more potent inhibitors of TS than is the monoglutamate. The polyglutamates are retained within cells, leading to a prolonged inhibitory action even in the absence of extracellular compound (Jackman et al., 1993). Tomudex thus is 500-fold more active in inhibiting cell growth than CB3717, despite being 20 times less potent as a TS inhibitor in enzyme assays (K$_i$, 60 nM) (Gibson et al., 1993; Lu et al., 1995). Tomudex has demonstrated activity in colorectal, breast, and pancreatic cancer and was approved in the U.K. for treatment of advanced colorectal cancer in August 1995. Also, phase III trials of tomudex in advanced colorectal cancer showed that tomudex is slightly superior to 5-FU with respect to anti-advanced colorectal cancer activity and therapeutic margin. BW1843U89 is an extremely potent, noncompetitive TS inhibitor in enzyme assays (Ki, 90 pM). As a TS-directed inhibitor, the monoglutamated form of BW1843U89 is as potent as the polyglutamated derivatives of tomudex in vitro studies. Similar to tomudex, growth inhibition could be reversed by thymidine alone, indicating that TS is its exclusive site of action. BW1843U89 does not require the RFC for the cellular entrance and is an excellent substrate for FPGS, but is only metabolized to a diglutamated form. The polyglutamation of this antifolate leads to retention in cells.

Drug resistance is a major obstacle to the successful use of chemotherapeutic agents in the treatment of neoplastic disease. For maintaining efficacious drug therapy, discovering new antitumor agents is an important goal. For drug resistance, investigations of naturally occurring resistance in model cell lines provides insights into the mechanisms that underlie innate clinical resistance in patients not previously exposed to these new drugs. The prior art is deficient in the lack of effective means of inhibiting the overcoming the resistance to TS inhibitors routinely encountered in anti-neoplastic therapy. The present invention fulfills this long-standing need and desire in the art.

SUMMARY OF THE INVENTION

The present invention randomly mutated HT1080 cells and subsequently selected drug-resistant clones with a high concentration of AG337. Secondly, site-directed mutagenesis was performed on three codons that code for amino acids that are folate-binding sites of human TS gene, based on the knowledge of three-dimension structures of TS. Using these two approaches, isolation and characterization of mutants of human TS conferring drug resistance to TS specific inhibitors were studied. The human TS mutants obtained have desirable properties including antifolate resistance, a high catalytic efficiency and good stability. This kind of TS variant is an excellent candidate for gene therapy approaches, namely to transfer drug resistance to human hemotopoietic progenitors, thus allowing dose-intense therapy in cancer patients by protecting normal cells and preventing dose-limiting myelotoxicity. Moreover, these mutants may be used as dominant selectable markers in therapeutic gene transfer protocol.

In one embodiment of the present invention, there is provided a mutated human thymidylate synthase, said mutated synthase differing from wild type thymidylate synthase of the amino acid sequence disclosed in Genbank Accession number NP001062 (SEQ ID No. 39) at amino acid residue 49, amino acid residue 52, amino acid residue 108, amino acid residue 221 or amino acid residue 225.

In another embodiment of the present invention, there is provided a cDNA encoding the mutated human TS of the present invention.

In yet another embodiment of the present invention, there is provided a DNA vector comprising: DNA encoding a mutated human TS of the present invention.

In still yet another embodiment of the present invention, there is provided a host cell transfected with the DNA vector of the present invention and wherein said host cell produces a mutated human TS.

In still yet another embodiment of the present invention, there is provided a method of decreasing the toxic effects of anti-neoplastic inhibitors of TS in an individual in need of such treatment, comprising the steps of: introducing a mutated human TS into cells of said individual; and returning said cells to said individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
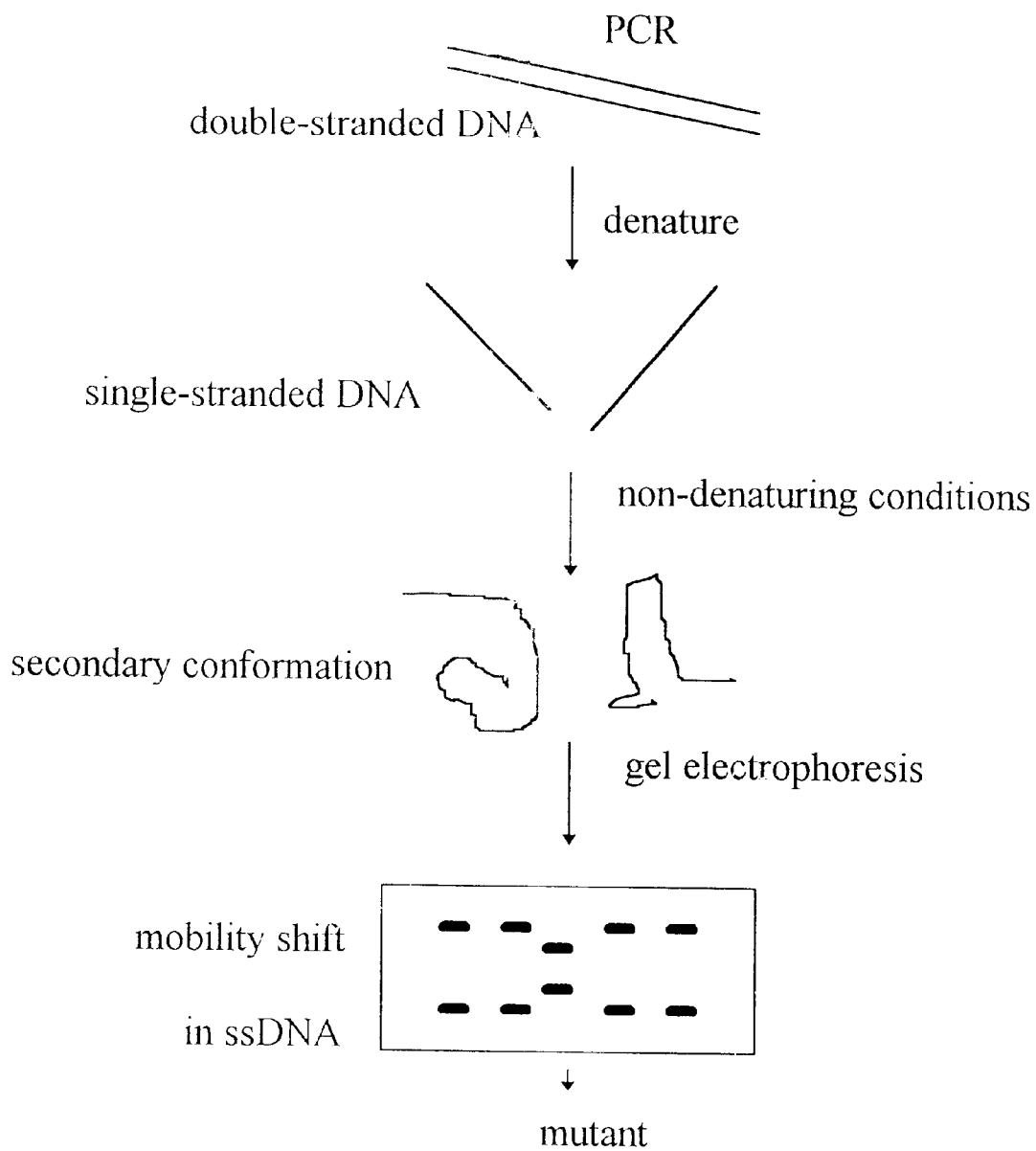
FIG. 1 shows the principle of single-strand conformation polymorphism (SSCP).

The present invention is directed to a mutated human thymidylate synthase, said mutated synthase differing from wild type thymidylate synthase of the amino acid sequence disclosed in Genbank Accession number NP001062 (SEQ ID No. 39) at amino acid residue 49, amino acid residue 52, amino acid residue 108, amino acid residue 221 or amino acid residue 225. In one mutated form, the amino acid residue 49 is mutated to an amino acid selected from the group consisting of asparagine and glycine. In another mutated form, amino acid residue 52 is mutated to serine. In another mutated form, amino acid residue 108 is mutated to an amino acid selected from the group consisting of alanine, phenylalanine, glycine, glutamic acid and asparagine. In another mutated form, amino acid residue 221 is mutated to an amino acid selected from the group consisting of phenylalanine, arginine, alanine, isoleucine and serine. In another mutated form, amino acid residue 225 is mutated to an amino acid selected from the group consisting of tryptophan, serine, leucine and tyrosine.

The present invention is also directed to a cDNA, said cDNA encoding a mutated human TS. The present invention is also directed to a DNA vector comprising: DNA encoding a mutated human TS. The present invention is also directed to a host cell transfected with the DNA vector wherein the host cell produces a mutated human TS. Preferably, the host cell is a mammalian hematopoietic cell and most preferably, the host cell is a peripheral blood stem cell.

The present invention is also directed to a method of decreasing the toxic effects of anti-neoplastic inhibitors of TS in an individual in need of such treatment, comprising the steps of: introducing a mutated human TS into cells of said individual; and returning said cells to said individual. Preferably, but not exclusively, the inhibitor of TS is selected from the group consisting of 5-fluorouracil, $N^{10}$-propargyl-5, 8-dideazafolic acid, N-(5-[N-(3,4-dihydro-2-methyl-4-oxoquinazolin-6-ylmethyl)-N-methyl amino-]-2-thenoyl)-L-glutamic acid, ZD1694 and BW1843U89.

The mutated human TSs may also be used as a selectable marker. For example, the present invention also provides a method of selecting among clones for the introduction of a non-selectable gene, comprising the steps of: (a) inserting the non-selectable gene into a DNA vector comprising DNA encoding a mutated human TS; (b) introducing the vector into cells of a type in which the non-selectable gene and the mutated human TS are expressed; and (c) selecting cells which are resistant to inhibition by anti-neoplastic inhibitors of TS.

The following examples are given for the purpose of illustrating various embodiments of the invention and are not meant to limit the present invention in any fashion.

EXAMPLE 1

Materials

The pCR-Script™ SK(+) cloning kit was purchased from Stratagene (La Jolla, Calif.). Transformer™ site-directed mutagenesis kit was purchased from CLONTECH Laboratories, Inc. (Palo Alto, Calif.). DOTAP was supplied by either Boehringer Mannheim (Indianapolis, Ind.) or by the liposome facility at Cornell Medical College (Dr. T. Scotto, New York, N.Y.). The GeneClean kit was obtained from BIO 101 Inc. (La Jolla, Calif.). DNA Sequencing kit and IPTG were purchased from United States Biochemical Corp. (Cleveland, Ohio). The bacterial expression plasmid pET-17(b and competent E. coli BL21(DE3) cells were from Novagen, Inc. (Madison, Wis.). The mammalian expression vector pcDNA3 was from Invitrogen, Corp. (San Diego, Calif.). DEAE-cellulose (DE52) was from Whatman (Clifton, N.J.), and Phenyl Sepharose CL-4B was from Pharmacia Biotech (Piscataway, N.J.). Bovine serum albumin (BSA) and Ethylmethanesulfonate (EMS) were supplied by Sigma Chemical Co. (St. Louis, Mo.). Fetal bovine serum and molecular weight standards were purchased from Gibco BRL (Gaithersburg, Md.). Bacterial growth and tissue culture media were supplied by an in house media unit. Restriction enzymes and DNA modifying enzymes were purchased from various suppliers (New England Biolabs, Bio-Rad, Promega, Stratagene, and Pharmacia). Ampli-Taq polymerase was purchased from Perkin-Elmer (Norwalk, Conn.). Chemicals were obtained from commercial sources and used without purification.

EXAMPLE 2

DNA Oligonucleotides

Oligonucleotide primers were synthesized by either IDT, Inc. (Coralville, Iowa) or Operon Technologies, Inc. (Alameda, Calif.). Prior to synthesis, all oligonucleotide sequences requested were checked with the computer program Oligo (Version 4.0.2., National Biosciences, Inc.) to optimize the primer design.

EXAMPLE 3

Source of Human TS Plasmid

Human recombinant TS cDNA of the sequence disclosed in Genbank Accession number NM001071 (SEQ ID No. 38) in bacterial expression vector pET-17(b), named pET-17 (bhTS), was provided by Dr. Frank Maley. In order to increase the levels of human TS protein expression in E. coli, the codon usage in the 5'-coding region of the gene was modified in this construct. The sequence ATGCCTGTGGC-CGGC (SEQ ID NO:1) was changed to ATGCTTGT-TGCIGGT (SEQ ID NO:2). These changes resulted in an alteration of Pro2 to Leu2. However, both in vivo and in vitro experiments proved that this substitution does not result in functional change for human TS enzyme.

EXAMPLE 4

Substrates and Inhibitors of Human TS Enzyme

AG337 was a gift of Agouron Pharmaceuticals, Inc. (San Diego, Calif.). $CH_2H_4$folate was synthesized by Schircks Laboratories (Switzerland). Tomudex was obtained from Zeneca (Macclesfield, United Kingdom). BW1843U89 was supplied by Glaxo-Wellcome (Research Triangle park, N.C.). dUMP, FdUrd, and FdUMP were purchased from Fisher Scientific (Fairlawn, N.J.). The concentrations of compounds were determined by UV absorbance, using appropriate extinction coefficients.

EXAMPLE 5

Cell Lines and Culture Conditions

Human fibrosarcoma HT1080 cells were obtained from the American Type Culture Collection (Rockville, Md.). Stock cultures of the parental cell line HT1080 and resistant sublines were maintained in RPMI 1640 medium supplemented with 10% fetal bovine serum, 2 mM L-glutamine, 100 µg/ml stretomycin, and 100 units/ml penicillin.

The TS-negative cell line FSthy21, a gift of Dr. T. Seno (Ayusawa et al., 1981), was originally established from mouse FM3 A cells. FSthy21 cells were grown in Eagle's minimum essential medium supplemented with 10% dialyzed fetal bovine serum, 2 mM L-glutamine, 100 µg/ml stretomycin, 100 units/ml penicillin, 1 µM reduced folate and 10 µM thymidine. Prototrophic transformant clones, derived from FSthy21 cells by transfection of wild-type or mutant human TS cDNAs, were cultured in the same medium as mentioned above without thymidine and reduced folate supplements.

EXAMPLE 6

Chemical Mutagenesis and Drug Selection: Ethylmethanesulfonate (EMS) Sensitivity of HT1080 Cells HT1080 cells were seeded into 6-well plates (100–300 cells/well). After overnight incubation to allow cell attachment, The cells were exposed with EMS for 18 hours, washed three times, and then incubated with EMS-free medium for a further 14 days. The range of EMS concentration tested was 100 to 1000 µg of EMS/ml of culture medium. Colonies formed (50 cells) were stained with crystal violet and counted. The concentration of EMS used for the random mutagenesis experiments was determined based on the number of colonies obtained in the EMS-treated test versus EMS concentrations (Sega, 1984; Fanin et al., 1993).

EXAMPLE 7

AG337 Sensitivity of HT1080

The optimum concentration of AG337 for selection of resistant clones was determined as follows. The human fibrosarcoma HT1080 cells were seeded into 6-well plates at 100 cells per well and incubated at 37° C. with complete medium. Various concentrations of AG337 were added after 24 hours. Drug-containing medium was changed every 4 days and surviving colonies were counted after 14 days of drug treatment. $IC_{50}$ values and the minimal concentration of AG337 that resulted in no colony formation in HT1080 cells were obtained by plots of colonies surviving versus AG337 concentrations.

EXAMPLE 8

Chemical Mutagenesis and Drug Selection

HT1080 cells ($4 \times 10^8$) growing in logarithmic phase were exposed 18 hr to EMS (400 µg/ml, a concentration that resulted in 80% inhibition of colony formation). The cells were washed and incubated a further 3 days in EMS-free medium to allow phenotypic expression. EMS-treated cells were subcultured at $6 \times 10^7$ cells/100 mm dishes, and then grown in the presence of 40 µM AG337 for 14 days. Forty-one individual clones obtained from EMS and AG337 sequentially treated cells were isolated with a ring cylinder and expanded into stable resistant sublines. Without EMS pretreatment, only 1 clone ($1 \times 10^8$ cells were plated as a control) survived exposure to 40 µM AG337.

EXAMPLE 9

Isolation of Total RNA

For Northern blot analysis and RT-PCR, the cells from HT1080 and 41 resistant sublines in log phase were harvested from 150-cm$^2$ tissue culture flasks, and RNA isolated using RNAzol (Bioteox lab., Inc.) according to the manufacturer's instructions. RNA pellets were resuspended in RNAse and DNAse free water and quantitated spectrophotometrically ($OD_{260}$=33 µg RNA/ml). The ratio of $OD_{260}/OD_{280}$ was greater than 1.8 in all of samples.

EXAMPLE 10

Reverse Transcription for cDNA Synthesis

Total RNA samples were heated in water for 5 minutes at 65° C. and then quickly cooled in an ice-water bath. For each sample, 5 µg of total RNA was adjusted to a final volume of 20 µl. The reaction mixture was composed of 50 mM Tris-HCl, pH 8.3; 50 mM potassium chloride; 6 mM magnesium chloride; 10 mM DTT; 10 µg random primer pd(N)$_6$; 50 units/ml RNAsin; 500 µM dNTPs; and 200 units AMV reverse transcriptase. The synthesis of first strand cDNA was performed at room temperature for 5 min. and then switched to 42° C. for 1 h after which the samples were used or stored at 20° C.

EXAMPLE 11

PCR Amplification, DNA-SSCP Screening and Sequence Analysis for Detection of Mutations: Polymerase Chain Reaction The PCR amplification was performed in DNA thermal cycler for 40 cycles in a 50 µl of total volume containing 5 µl of the reaction mixture of reverse transcription as the template, 50 pmols of each primer (primer sequences used for PCR amplification were sense 5-CACAGGAGCGGGACGCCGAG-3' (SEQ ID NO:3) and antisense 5'-AACAGCCATTTCCATTTTAATAGT-3' (SEQ ID NO:8), which cover a 890 bp of fragment from nt 50 to the C-terminus of the human TS gene), 80 µM of each of the four dNTPs, 1×PCR buffer and 1 unit of Taq DNA polymerase. After 1 cycle of initial denaturing at 94° C. for 10 min., annealing at 55° C. for 1 min., and extension at 72° C. for 2 min., 40 cycles of 94° C. for 1 min., 55° C. for 1 min., and 72° C. for 2 min were performed. The PCR product corresponding to a 890 bp fragment was separated on a 1.2% TAE agarose gel and identified with ethidium bromide. The amplified DNA fragments were purified using a Gene Clean kit. The sequences of oligonucleotide primers which were used in various experiments such as PCR amplification, DNA-SSCP and sequence analysis are described in TABLE 1.

TABLE 1

The Sequences of Oligonucleotides Used for PCR Amplification. DNA-SSCP Screen and Sequence Analysis

| Oligonucleotide Reference | Sequence of Oligonucleotide 5' → 3' | Anneals to human TS |
|---|---|---|
| hTS-1A* (SEQ ID NO: 3) | CACAGGAGCGGGACGCCGAG | nt 50 to 69 |
| hTS-1B (SEQ ID NO: 4) | CAAAAGTCTCGGGATCCATT | nt 354 to 334 |
| hTS-2A (SEQ ID NO: 5) | GAGCTGTCTTCCAAGGGAGTGA | nt 298 to 319 |
| hTS-2B (SEQ ID NO: 6) | TCTCTGGTACAGCTGGCAGGACAG | nt 645 to 622 |
| hTS-3A (SEQ ID NO: 7) | CTGCCAGTTCTATGTGGTGAACAGTG | nt 594 to 616 |
| hTS-3B (SEQ ID NO: 8) | AACAGCCATTTCCATTTTAATAGT | nt 939 to 915 |
| hTS-4A (SEQ ID NO: 9) | TACCTGGGGCAGATCCAACAC | nt 97 to 117 |
| hTS-4B (SEQ ID NO: 10) | TTCATCTCTCAGGCTGTAGCGCG | nt 210 to 188 |
| hTS-5A (SEQ ID NO: 11) | TCAGATTATTCAGGACAGGGAGTTG | nt 451 to 475 |
| hTS-5B (SEQ ID NO: 12) | ATGGTGTCAATCACTCTTGCAG | nt 503 to 481 |
| hTS-6A (SEQ ID NO: 13) | GGGAGATGCACATATTTACCTGAA | nt 756 to 779 |
| hTS-6B (SEQ ID NO: 14) | TCTGGGTTCTCGCTGAAGCT | nt 822 to 803 |

*Capital A represents sense, and B represents antisense

EXAMPLE 12

Single-Stranded Conformation Polymorphism (SSCP) Analysis

For DNA-SSCP analysis, small human TS fragments (150–260 bp) were obtained by PCR amplification of TS cDNA using 6 pairs of TS specific primers (see TABLE 2). The reaction mixture containing 1 $\mu$Ci [$\alpha$-$^{32}$P]dCTP and a small volume (3 $\mu$l) of final PCR products was subsequently mixed with 10 $\mu$l of loading buffer containing 96% formamide. Samples were denatured at 94° C. for 3 min., chilled on ice for at least 5 min. and 2 $\mu$l was loaded onto a 6–8% non-denaturing polyacrylamide gel with or without 10% glycerol. Gels were electrophoresed at 10 W for 6–8 hours at 4° C., using 0.5 (Tris-borate-EDTA buffer. The separated single-strand DNA fragments were visualized by autoradiography.

An alternative method (called nonisotopic SSCP) was also utilized, in which the single-strand DNA bands are detected by ethidium bromide staining instead of autoradiography. At least 40 ng (20 $\mu$l) of amplified DNA fragments was denatured by addition of 1 $\mu$g 0.5 M NaOH, 10 mM EDTA at 42° C. for 5 minutes. Just before loading, 1 $\mu$l of formamide containing 0.5% bromophenol blue and 0.5% xylene cyanol were added. Non-denaturing gels (1.5 mm thick, 6–8% polyacrylamide), with and without 5% glycerol, were made in a standard vertical gel apparatus. Gels, using 0.5(TBE as running buffer, were electrophoresed at 15 (V/cm of gel) for 4 hours and temperature was maintained at 4° C. by circulating cold water. Finally, SSCP gels were neutralized and stained in 0.5×TBE containing 0.5 $\mu$g/ml ethidium bromide for band observation. The principles of SSCP for detection of mutations is presented by FIG. 1.

EXAMPLE 13 pCR-Script™ SK(+) Cloning

The RT-PCR fragments with putative mutations in human TS were subsequently subcloned into pCR-Script™ SK(+) vector, which permits the efficient cloning of PCR fragments with a high yield and a low rate of false positives. After ligation and transformation, the positive white colonies containing human TS fragments were chosen for further miniprep isolation and sequence analysis.

EXAMPLE 14

DNA Sequence Analysis

Sequence analysis was performed by the dideoxy chain termination method with $\alpha$-$^{35}$S dATP using modified T7 DNA polymerase according to the manufacture's instructions. Templates were either PCR products or alkali-denatured plasmid DNA. The plasmid ligated by pCR-Script™ SK(+) Cloning vector with human TS fragments exhibiting abnormal mobility on SSCP gels were sequenced by two commercial designed primers [M3 (−20) and M13 reverse]. Direct sequencing of the PCR products was carried out using single-stranded DNA products denatured by NaOH as templates and designed human TS oligonucleotides (see TABLE 1) as sequencing primers. After completion of the sequencing reaction, the products were loaded on a 8% polyacrymide urea gel, which was electrophoresed at 80 W for 2–3 hours after which the gel was dried and exposed to film. Mutations were verified by comparison of wild-type control lanes

EXAMPLE 15

Studies of AG337-Resitant Cell Lines: Whole Cell TS Assay

Resistance to TS inhibitors was evaluated using the whole cell TS assay for several AG337-resistant sublines and parental cell line HT1080 as a control. Cell suspensions ($2\times10^6$ cells/ml) were exposed for 4 hours to different concentrations of either an antifolate drug (AG337, tomudex) or 5-fluoro-2'-deoxyuridine (FdUrd). For the absence of TS inhibitors, cells convert 2'-[5-$^3$H]-deoxyuridine to dTMP, releasing $^3$H$_2$O into the medium. The rate of dTMP synthesis in the presence or absence of drug was assessed at 0, 15, 30, 40 minutes, by measurement of [3H]$_2$O release by charcoal-TCA (trichloroacetic acid) separation of $^3$H$_2$O from nucleosides and nucleotides. Radioactivity was quantitated using a liquid scintillation counter (Beckman LS5).

EXAMPLE 16

Northern Blot Analysis

Fifty μg samples of RNA were subjected to electrophoresis through 1.5% denaturing formadehyde-agarose gels in 1×MOPS buffer, running at constant volts (5 V/cm of gel). The gels were washed in water and 10×SSC and then transferred onto a nitrocellulose membrane. After blotting, RNA on the membrane was immobilized by UV cross-linking, prehybridized for 24 hours at 42° C., and then hybridized at the same temperature for a further 18 hours. The human TS probe, which was $^{32}$P-labeled by random primer DNA labeling kit, was a 950 bp gel-purified fragment of human TS cDNA cleaved from the pET-17xbhTS plasmid with NdeI and HindIII restriction enzymes. Ribosomal phosphoprotein 36B4 cDNA was used as a loading control. After hybridization, the blots were washed and visualized by autoradiography.

EXAMPLE 17

Western Blot Analysis

Protein concentrations in cell extracts were determined by the Bradford assay using Bio-Rad dye reagent. Protein extracts (100 μg) were boiled for 5 minutes, loaded on a 12.5% polyacrylamide-SDS gel, and then electrophoresed at constant current (30 mA/gel). The gel was transferred onto a nitrocellulose membrane, which was then blocked overnight with 5% milk in 0.1 M Tris, pH 7.4. To detect TS, a rabbit anti-human TS polyclonal antibody at a 1:1000 dilution in the same buffer as above was added and the blots were washed with 0.1 M Tris, pH 7.4. The goat anti-rabbit IgG antibody at a dilution of 1:500 was used as the secondary antibody. Human TS proteins were visualized by the ECL method. The polyclonal antibody for human TS was a gift of Dr. Frank Maley.

An alternative more rapid hydrophobic blotting procedure was also used by utilizing immobilon-P membrane instead of the nitrocellulose membrane. After transfer, the membrane was soaked in 100% methanol for 2 min. and then allowed to air dry for 15 minutes. The completely dried membrane was incubated with the TS antibody in the buffer (1×saline, 1% non-fat milk and 0.05% Tween-20) at 4° C. for 1 hr with gently shaking, washed with buffer (lxsaline and 0.05% Tween-20) at room temperature for 2 min. twice, and incubated with goat anti-rabbit IgG antibody in the same buffer and incubated, following washing, the protein bands were visualized.

EXAMPLE 18

Construction of a Mammalian Expression Vector for Human TS

The vector pcDNA3 under T7 promoter control was used to construct a mammalian expression system for human TS. The construction of the plasmid containing recombinant human TS cDNA of the sequence disclosed in Genbank Accession number NM001071(SEQ ID No. 38) was performed by digestion of pET-17xbhTS with NdeI and HindIII to generate a 950 bp fragment containing a full cDNA sequence of human TS. The reaction mixture was treated with T4 DNA polymerase to make blunt ends and isolated by electrophoresis on a 1.2% TAE agarose gel. This 950 bp DNA fragment was cut out and then purified by use of the GeneClean kit. The pcDNA3 expression vector was digested with EcoRV and the sole DNA fragment (5.4 kb) was extracted. The pcDNA3 fragment was then mixed with a 10-fold excess of the 950 bp fragment in the presence of T4 ligase and incubated at 14° C. overnight. The ligation mixture was then directly transformed into competent DH5αcells. A pcDNA3hTS plasmid with correct size (6.4 kb) and orientation was confirmed by restriction mapping and sequencing.

EXAMPLE 19

Site-Directed Mutagenesis

The Transformer™ site-directed mutagenesis kit was used to obtain point mutations in human TS (2nd version, Clontech). This single-strand based technique takes advantage of the difference in the transformation efficiency between circular and linear DNA. Twenty-two oligonucleotides were designed and synthesized. The last one (TABLE 2) is a selection primer that contains a unique KspI restriction site instead of the unique SmaI restriction site on the pcDNA3 vector. The other 22 primers were designed to obtain mutants of the human TS gene at the targeted site. Mutant human TS cDNA was obtained by annealing one mutagenic and one selection primers to the alkali-denatured single-strand pcDNA3hTS plasmid. The second strand DNA was synthesized by T4 DNA polymerase and cycled by T4 DNA ligase using the pcDNA3hTS as a template and the two annealed primers. The reaction mixture, which contained circular DNA with one mutated and one unchanged strand, was digested with SmaI and then transformed into DNA repair-deficient BMH 71-18 mutS cells. Transformed bacteria cells were grown overnight and the mixed plasmids were isolated by miniprep. In order to increase the transformation efficiency of the circular plasmid containing the mutant human TS, the plasmid mixture was linearized with SmaI again and subsequently transformed into *E. coli* DH5 (competent cells and plated. After double SmaI digestion and double transformations, the resulting colonies were screened using KspI digestion that only cuts newly synthesized plasmids. Plasmids with putative point mutations in human TS were examined further by restriction mapping and DNA sequencing.

TABLE 2

Oligonucleotides Used for Site-Directed Mutagenesis
(Nucleotide Underlined were those used to change
the codon)

| Position in hTS and created mutation | Mutagenic oligonucleotide sequences 5' → 3' | Reference number & SEQ ID NO. | |
|---|---|---|---|
| Phe$^{225}$→Trp$^{225}$ | CGGTGTGCCTTGGAACATCGCCAG | 162 | (SEQ ID NO: 15) |
| Phe$^{225}$→Ser$^{225}$ | CGGTGTGCCTCCCAACATCGCCAG | 163 | (SEQ ID NO: 16) |
| Phe$^{225}$→Leu$^{225}$ | CTCGGTGTGCCTCTCAACATCGCC | 83 | (SEQ ID NO: 17) |
| Phe$^{225}$→Tyr$^{225}$ | CGGTGTGCCTTACAACATCGCCAG | 84 | (SEQ ID NO: 18) |
| Leu$^{221}$→Phe$^{221}$ | GGAGACATGGGCTTCGGTGTGCCTT | 164 | (SEQ ID NO: 19) |
| Leu$^{221}$→Arg$^{221}$ | GAGACATGGGCCGCGGTGTGCCTTTC | 165 | (SEQ ID NQ: 20) |
| Leu$^{221}$→Ala$^{221}$ | GAGACATGGGCGCGGTGTGCCTT | 85 | (SEQ ID NO: 21) |
| Leu$^{221}$→Ile$^{221}$ | GAGACATGGGCATCGGTGTGCC | 86 | (SEQ ID NO: 22) |
| Leu$^{221}$→Ser$^{221}$ | GAGACATGGGCAGCGGTGTGCCTT | 87 | (SEQ ID NO: 23) |
| Ile$^{108}$→Ala$^{108}$ | GGGAGTGAAAGCCTGGGATGCC | 175 | (SEQ ID NO: 24) |
| Ile$^{108}$→Phe$^{108}$ | CAAGGGAGTGAAATTCTGGGATGCCA | 176 | (SEQ ID NO: 25) |
| Ile$^{108}$→Gly$^{108}$ | GGGAGTGAAAGGCTGGGATGCC | 270 | (SEQ ID NO: 26) |
| Ile$^{108}$→Gly$^{108}$ | GGGAGTGAAAGAGTGGGATGCC | 271 | (SEQ ID NO: 27) |
| Ile$^{108}$→Asn$^{108}$ | GGGAGTGAAAAACTGGGATGCC | 272 | (SEQ ID NO: 28) |
| Asp$^{49}$→Asn$^{49}$ | GTCAGGAAGGACAACCGCACGGGCA | 923 | (SEQ ID NO: 29) |
| Asp$^{49}$→Gly$^{49}$ | TCAGGAAGGACGGCCGCACGGGCAC | 928 | (SEQ ID NQ: 30) |
| Thr$^{51}$→Ala$^{51}$ | AAGGACGACCGCGCGGGCACCGCA | 924 | (SEQ ID NQ: 31) |
| Lys$^{47}$→Glu$^{47}$ | GCGGCGTCAGGGAGGACGACCGC | 925 | (SEQ ID NO: 32) |
| Arg$^{50}$→Cys$^{50}$ | AGGAAGGACGACTTCACGGGCACCG | 926 | (SEQ ID NO: 33) |
| Gly$^{52}$→Ser$^{52}$ | GACGACCGCACGAGCACCGGCACCCT | 927 | (SEQ ID NO: 34) |
| Phe$^{59}$→Leu$^{59}$ | ACCCTGTCGGTACTCGGCATGCAGG | 75 | (SEQ ID NO: 35) |
| Gln$^{214}$→Arg$^{214}$ | TGCCAGCTGTACCGGAGATCGGGAGA | 76 | (SEQ ID NO: 36) |
| PcDNA3 (SmaI→KspI)* | CAAAAAGCTCCGCGGAGCTTGTATA | 161 | (SEQ ID NO: 37) |

EXAMPLE 20

Expression of TS Variants and Cytotoxicity Assay: Transfection of TS-Negative Cells with Wild-Type and Mutant Human TS cDNA's The mouse TS-negative FSthy21 cells were used as the host for DNA transfections. This cell line, which is a TS-deficient derivative of mouse FM3A cells, was routinely maintained in MEM medium supplemented with 10% fetal bovine serum and 10×10$^{-5}$ M thymidine. Transfections were performed by DOTAP, using 10 μg of DNA/culture. Four days after transfection, cells were placed in selective medium, which contain no thymidine and reduced folate. Colonies having the ability to grow in the absence of thymidine were pooled and propagated as a mass culture.

EXAMPLE 21

Growth Inhibition Assay for Transfected Cells

Logarithmically growing suspension mouse TS-20 negative FSthy21 cells transfected with wild-type or variant human TS cDNA were seeded in 96-well plates at 1,000 cells/well in 180 μl of complete medium. Two hours later, drug (tomudex, AG337, BW1843U89 or FdUrd) was added and the cells were grown in drug-containing medium for an additional 7 days. Cell viability was measured by the alamar Blue™ assay. This method incorporates an oxidation-reduction (REDOX) indicator that both fluoresces and changes color in response to chemical reduction of growth medium resulting from cell growth. To above 96-well cultured cells, 25 μl of Alamar Blue (Alamar, Sacramento, Calif.) (10% of incubation volume) were added according to the manufacturer's instructions. The culture 96-well plates were then incubated at 37° C. for 4 hours. Viable cells induce chemical reduction of the media which results in a change in REDOX color from blue to red. The intensity of red color (and fluoresces) is proportional to the viable cells. After incubation, fluorescence is was read at 530–560 nm excitation wavelength and 590 nm emission wavelength by an automated plate reader (model EL340; Bio-Tek). Drug concentrations needed to reduce cell growth by 50% (IC$_{50}$ values) were determined graphically by plotting of cell growth verses inhibitor concentration.

EXAMPLE 22

TS Purification and Characterization: Construction of Bacteria Expression Vectors with Human TS Variants Human TS variants (I108A, F225W, G52S and D49G) selected for enzyme kinetic characterization, were recloned into the protein expression vector pET-17(b. DNA fragments covering the entire mutant human TS cDNA were amplified using pcDNA3hTS* as the templates using two designed primers. The 5'-primer contains a created NdeI restriction site and the 3'-primer has XhoI site. After PCR amplification, the reaction mixture was digested with the NdeI and XhoI enzymes and the desired DNA fragment (950 bp) was inserted to the corresponding sites of pET-17b vector. The correct construction of pET-17bhTS* was verified by plasmid mapping and sequence analysis.

EXAMPLE 23

Expression of Recombinant Mutant Human TS and Preparation of Bacterial Crude Extract The pET-17xbhTS* plasmid (wt or mutant TSs) was used to transform into *E. coli* strain BL21 (DE3). Bacteria containing plasmids were grown at 30° C. in 1 liter of tryptone phosphate medium [2% bacto-tryptone, 1.5% yeast extract, 0.2% sodium phosphate (dibasic), 0.1% potassium phosphate (monobasic), 0.8% sodium chloride and 0.2% glucose] supplemented with 100 μg/ml of ampicillin (Moore et al., 1993). When the $OD_{600}$ reaches 0.6–0.8, 1 mM of IPTG was added to induce synthesis of the human protein. After 5 hours of incubation, bacteria were harvested and then washed in TNE buffer (10 mM Tris-HCl, pH 8.0, 150 mM NaCl, 10 mM EDTA). The harvested bacteria were resuspended in TNE buffer containing 20 mM BME and sonicated (10×30 sec, set 50) on ice. The debris was removed by centrifugation at 37 000×g for 30 minutes at 4° C. to obtain the soluble extract. The supernatants were assayed for TS activity using the spectrophotometric assay and analyzed by SDS-PAGE. The expressed human TS protein was visualized by staining with Coomassie Blue.

EXAMPLE 24

Purification of Wild-Type and Variants of Human TS

The wt and various mutant TSs were induced with 1 mM IPTG for 5 hours at which point the enzyme was induced to about 10%–15% of the soluble protein. All of the purification procedures were performed at 0–4° C. and yielded protein of high purity for kinetic characterization. Step 1: Streptomycin Treatment. A 5% solution of streptomycin sulfate was added the extract (15 ml/100 ml). The suspension was stirred for 20 min. and then centrifuged at 27 000×g for 30 min. Step 2: Ammonium Sulfate. The supernatant fraction from the previous step was brought to 30% saturation ammonium sulfate with solid ammonium sulfate, which was stirred for 20 min. and centrifuged at 27 000×g for 30 min., and the pellet discarded. The resulting solution was then brought to 80% saturation and centrifuged as before. The precipitate was dissolved in 10 ml of buffer (10 mM potassium phosphate, pH 7.4, 20 mM BME) and dialyzed overnight against the same buffer (2 liters). Step 3: Ion-Exchange Cellulose Chromatography. The dialyzed solution (100 to 200 mg of protein) was loaded to 1.5×8-cm column of DE-52 equilibrated with 10 mM $KH_2PO_4$, pH 7.4, 20 mM BME. The column was washed with the loading buffer at 1 ml/min. until no protein peaks were eluted and the concentration of potassium phosphate changed to 25 mM. TS-containing fractions eluting with 50 mM $KH_2PO_4$, pH 7.4 20 mM BME were pooled and then precipitated with solid ammonium sulfate to 80% saturation and centrifuged at 27 000×g for 30 min. The ammonium sulfate precipitate with human TS are stable stored at −20° C. Step 4: Phenyl-Sepharose CL-4B Chromatography. The pellet from the above step was dissolved in 20 mM $KH_2PO_4$, pH 7.4 0.25 mM EDTA, 20 mM BME containing 0.8M ammonium sulfate and loaded onto a 1.5×8-cm column of phenyl-Sepharose CL-4B equilibrated with the same buffer. The column was washed with 200 ml of the loading buffer and TS-containing fractions eluted with 500 ml of a decreasing linear gradient of ammonium sulfate from 0.8 mM to 0. Fractions were concentrated by centrifugal ultrafiltration and precipitated with solid ammonium sulfate and stored at −80° C. until use. TS purity was demonstrated by 12% SDS-PAGE.

EXAMPLE 25

Enzyme Assays for Wild-Type and Mutant Human TSs

TS activity was monitored spectrophotometrically at 340 nm as described (Wahba et al., 1961). Activity was determined at 30° C. The assay mixture contained 50 mM Tris.HCl, pH 7.4, 25 mM $MgCl_2$, 6.5 mM formadehyde, 1 mM EDTA, 75 mM BME and 100 μM dUMP, $CH_2H_4$folate (100 μM) was added to initiate the reaction. Black cuvettes lacked $CH_2H_4$folate. A unit of activity is defined as the amount of enzyme required to convert 1 μmol of dUMP to dTMP/minutes at 30° C. Protein was determined from $OD_{280}=0.87\times10^5$ $M^{-1}$ $cm^{-1}$, which is equivalent to 1.43 $OD_{280}$/mg of protein.

EXAMPLE 26

$K_m$ of $CH_2H_4$folate

Michaelis constants ($K_m$'s) for $CH_2H_4$folate and dUMP were determined from initial velocity measurements, which were obtained by measuring the change in $OD_{340}$ with a Shimadzu UV-2101 PC spectrophotometer. For determination of $K_m$ of $CH_2H_4$folate, the concentration of dUMP was fixed at 200 μM while $CH_2H_4$folate was varied between 10 and 400 μM. For determination of $K_m$ of dUMP, $CH_2H_4$folate was present at a concentration of 3 mM, and dUMP was varied between 1 to 300 μM. Steady-state kinetic parameters were subsequently obtained by a nonlinear least-squares fit of the data to the Michaelis-Menten equation using a computer program. The $k_{cat}$s were calculated by dividing $V_{max}$ by the estimated concentration of enzyme used in the reaction.

EXAMPLE 27

$K_i$ of Antifolates and FdUrd

Inhibition constants ($K_i$'s) were determined from the steady-state inhibition reaction rates for mixtures of enzyme, dUMP, $CH_2H_4$folate and inhibitor. A high fixed $CH_2H_4$folate concentration (300 μM) and variable antifolate concentrations were used to measure the inhibition produced by tomudex, AG337 and BW1843U89 while a constant dUMP concentration and varied FdUMP concentrations were applied for FdUMP.

EXAMPLE 28

AG337 in Human Sarcoma HT1080 Cells after Exposure to Ethylmethanesulfonate

The development of drug resistance is a major limiting factor to successful chemotherapy of cancer in humans. Cells in culture have served as an useful tool for the study of the mechanisms of drug resistance. Of the novel TS-targeted antifolates such as tomudex, BW1843U89 and AG337, tomudex has been intensively studied in cultured cell lines and several factors associated with resistance to tomudex have been described, including decreased drug uptake, defective intracellular polyglutamylation as well as elevation of TS protein (Lu et al., 1995). Mutations in the TS gene leading to expression of an altered enzyme with reduced affinity for tomudex, BW1843U89 or AG337 has not yet been reported.

The present invention isolated a mutant human TS which when transfected into bone marrow progenitor cells confers resistance to these TS specific antifolates. In addition, the present invention evaluated mechanisms of resistance to these novel TS inhibitors. In order to increase the possibility of obtaining human TS mutations leading to antifolate resistance, human sarcoma HT1080 cells were exposed to ethylmethanesulfonate (EMS), a monofunctional alkylating agent, followed by AG337 selection. Similar procedures were used to generate a number of resistant clones to TMTX, a DHFR inhibitor. Both DHFR gene amplification and mutations in DHFR were found (Fenin et al., 1993). The lipophilic TS inhibitor AG337 rather than tomudex or BW1843U89 was used as the selective drug since it does not utilize the reduced folate carries for transport and is structurally precluded from polyglutamation, thus probably narrowing the causes of drug resistance to TS gene amplification or TS mutations. Also, the development of drug-resistant sublines by random mutagenesis following single-step drug selection might increase the possibility of obtaining TS mutants that demonstrate decreased affinity for AG337 and other TS antifolate inhibitors.

A concentration of 400 µg of EMS/ml of culture medium was chosen for HT1080 cell exposure, which resulted in 80% inhibition of colony formation. The $IC_{50}$ of AG337 for HT1080 cells is 2.1 µM, which was obtained from drug cytotoxicity assay. A high concentration of 40 µM (19-fold of the $IC_{50}$) was used to select resistant clones based on the solubility of this drug. Total forty-one AG337-resistant colonies were obtained following EMS mutagenesis. In contrast, only 1 colony survived from $1\times10^8$ cells exposed to the same concentration of AG337 without EMS pretreatment. Thus, as expected, EMS exposure dramatically enhanced the frequency of AG337-resistant colonies (10-fold). Stable resistant colonies were continued in the presence of drug to expand to cell lines for further analysis.

EXAMPLE 29

Single-Stranded Conformation Polymorphism Analysis of Resistant Cell Lines to Detect TS Mutants For analysis of TS mRNA by the PCR-SSCP method, total cellular RNAs from a parental and 42 resistant cell lines (1 from the control experiment) expanded from individual colonies were transcribed into cDNA's using reverse transcriptase. The single-stranded cDNA fragments thus obtained were amplified by the PCR to double-stranded DNA fragments (890 bp) using a set of two appropriate oligonucleotide primers (hTS-1A and hTS-3B), which have nucleotide sequences complementary to the coding region (nt 50 to 69 and nt 939 to 915, respectively) of the TS mRNA. Human TS has unique 27 amino acids encoded by over 70% of G and C at the amino terminus, causing the problem for designing a specific binding primer much closer N-terminus than hTS-1A. Thus it is possible that mutations in the first 70 nucleotides was missed. TS cDNA fragments obtained by RT-PCR were amplified again by 6 pairs of TS specific primers to generate smaller fragments of DNA. The six regions of the TS cDNA amplified are indicated in TABLE 3, the fragments with nucleotide lengths of 161 to 259 base pairs obtained being designated as A to F. These six regions, which overlapped each other and covered the most coding sequences of the TS cDNA of about 890 bp, were subjected to SSCP analysis.

TABLE 3

DNA Fragments Amplified by Six-Pair of Primers for SSCP Analysis

| Primer Pair | PCR Product | Region Detected by SSC | Region # |
|---|---|---|---|
| hTS-1A/hTS-4B | 161 bp (nt 50–210) | nt 70–187 (118 bp) | A |
| hTS-4A/hTS-1B | 258 bp (nt 97–354) | nt 118–333 (216 bp) | B |
| hTS-2A/hTS-5B | 196 bp (nt 298–503) | nt 320–480 (161 bp) | C |
| hTS-5A/hTS-2B | 195 bp (nt 451–645) | nt 476–621 (146 bp) | D |

TABLE 3-continued

DNA Fragments Amplified by Six-Pair of Primers for SSCP Analysis

| Primer Pair | PCR Product | Region Detected by SSC | Region # |
|---|---|---|---|
| hTS-3A/hTS-6B | 229 bp (nt 594–822) | nt 617–802 (186 bp) | E |
| hTS-6A/hTS-3B | 184 bp (nt 756–939) | nt 780–914 (135 bp) | F |

Figure 2:
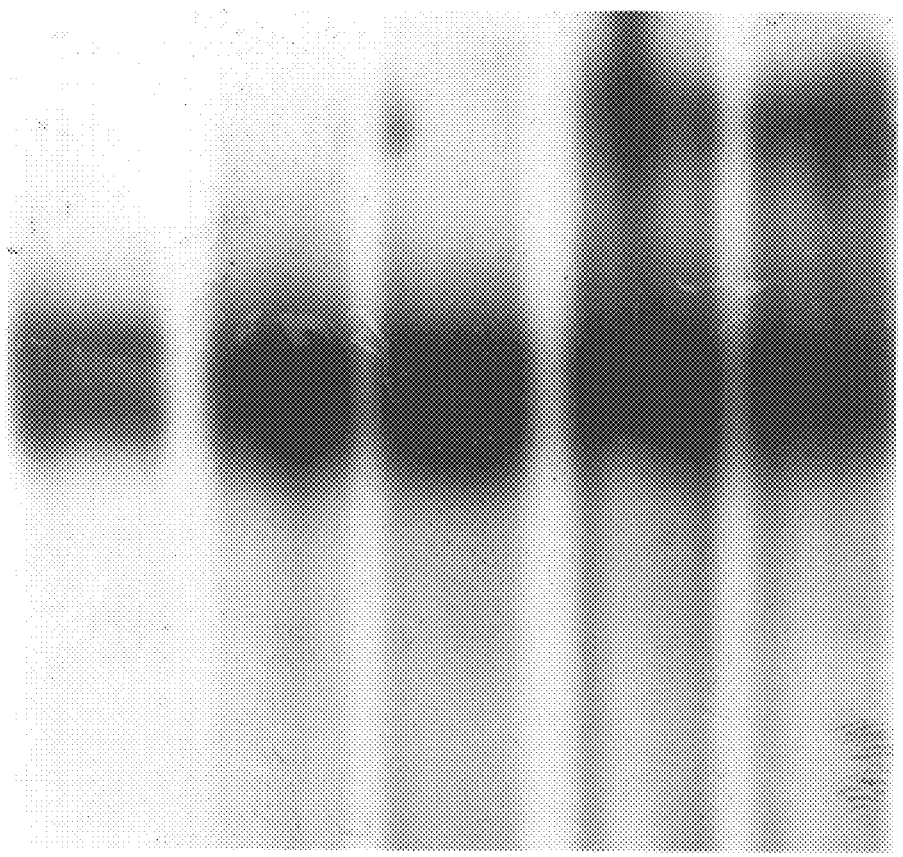
FIG. 2 shows an autoradiogram of SSCP analysis of human TS gene mutations in AG337-resistant cells. Amplified DNA fragments by RT-PCR corresponding to region A were denatured by heating and electrophoresis was performed in 8% polyacrylamide gel containing 5% glycerol at constant 30 W at 4° C. Lane 1: control HT1080 cells; Lane 2 to Lane 5: AG337-resistant cells. Fragments with mobility shift in addition to wild-type bands are observed in Lane 4 and Lane 5, suggesting mutations in human TS gene from nucleotide coding 70 to 187 for HT1080/1b and HT1080/2b.

After PCR amplification, DNA fragments were analyzed on SSCP gels. The separated single-strands DNA were visualized by either isotopic [$(\alpha^{32}P)$dCTP labeling or ethidium bromide staining. Different running temperatures with or without 10% glycerol were tested to observe abnormally migrating SSCP bands to define optimal conditions. The results of DNA-SSCP analysis for TS cDNA are summarized on TABLE 4. Nine of 41 resistant cell lines (HT1080/1a, 2a, 1b, 2b, 1c, 2c, 1d, 2 d, and 6e) showed single-stranded DNA fragments with mobility shifts in addition to wildtype bands (see FIG. 2), indicating possible structural changes in those fragments due to mutations in the TS gene.

TABLE 4

DNA-SSCP Analysis of HT1080 and Resistant Cell Lines

| | A | B | C | D | E | F |
|---|---|---|---|---|---|---|
| H1080 | N[3] | N | N | N | N | N |
| HT1080/A[1] | N | N | N | N | N | N |
| HT1080/1a[2] | N | N | N | N | N | N |
| HT1080/2a | N | N | N | N | N | N |
| HT1080/1b | B.S.[4] | B.S. | N | N | B.S. | B.S. |
| HT1080/2b | B.S. | N | N | N | N | N |
| HT1080/3b | N | N | N | N | N | N |
| HT1080/4b | N | N | N | N | N | N |
| HT1080/5b | N | N | N | N | N | N |
| HT1080/6b | N | N | N | N | N | N |
| HT1080/7b | N | N | N | N | N | N |
| HT1080/1c | B.S. | N | N | N | N | N |
| HT1080/2c | B.S. | N | N | N | N | N |
| HT1080/3c | N | N | N | N | N | N |
| HT1080/4c | N | N | N | N | N | N |
| HT1080/5c | N | N | N | N | N | N |
| HT1080/6c | N | N | N | N | N | N |
| HT1080/7c | N | N | N | N | N | N |
| HT1080/1d | B.S. | N | N | N | N | N |
| HT1080/2d | B.S. | N | N | N | N | N |
| HT1080/1e | B.S. | N | N | N | N | N |
| HT1080/2e | B.S. | N | B.S. | N | N | B.S. |
| HT1080/3e | N | N | N | N | N | N |
| HT1080/4e | N | N | N | N | N | N |
| HT1080/5e | N | N | N | N | N | N |
| HT1080/6e | N | B.S. | N | N | N | N |
| HT1080/7e | N | N | N | N | N | N |
| HT1080/8e | N | N | N | N | N | N |
| HT1080/9e | N | N | N | N | N | N |
| HT1080/10e | N | N | N | N | N | N |
| HT1080/11e | N | N | N | N | N | N |
| HT1080/1f | N | N | N | N | N | N |
| HT1080/2f | N | N | N | N | N | N |
| HT1080/3f | N | N | N | N | N | N |
| HT1080/4f | N | N | N | N | N | N |
| HT1080/5f | N | N | N | N | N | N |
| HT1080/6f | N | N | N | N | N | N |
| HT1080/7f | N | N | N | N | N | N |
| HT1080/8f | N | N | N | N | N | N |
| HT1080/9f | N | N | N | N | N | N |
| HT1080/10f | N | N | N | N | N | N |
| HT1080/11f | N | N | N | N | N | N |
| HT1080/12f | N | N | N | N | N | N |

TABLE 4-continued

DNA-SSCP Analysis of HT1080 and Resistant Cell Lines

| A | B | C | D | E | F |
|---|---|---|---|---|---|

[1]This cell line was obtained from the control experiment. The other 41 cell lines labeled by number plus a to f were from random mutagenesis experiment
[2]small a to f represent different plates).
[3]N indicates that this fragment no band shifts.
[4]B.S. indicates that this DNA fragment had band shifts.

EXAMPLE 30

Tritium Release Assay for TS Activity in Whole Cells

The effect of AG337 on whole cell in situ TS activity was measured by the tritium release assay in HT1080 cells and several resistant cell lines with putative mutations. The cell lines HT1080/1b, HT1080/2b, HT1080/1c, HT1080/2c, HT1080/1d, HT1080/2d and HT1080/6e were resistant to AG337. At the minimal concentration of AG337 that resulted in no detectable TS activity for HT1080, TS activity in the above mentioned resistant cell lines was not totally inhibited, showing those cells were less sensitive to AG337 than the parental cells. This method provided a rapid qualitative confirmation of whether or not a cell line is resistant to AG337.

EXAMPLE 31

Northern Blot Analysis

Figure 3:
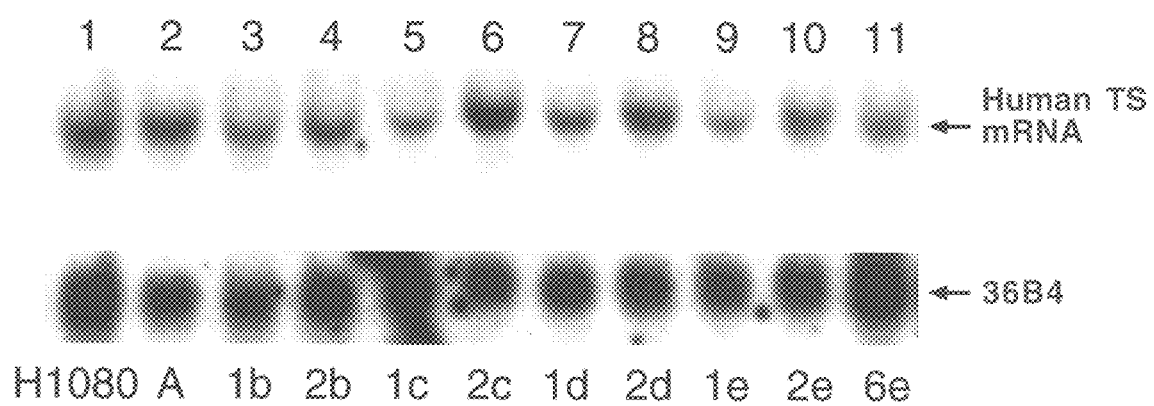
FIG. 3 shows the northern blot analysis of total RNA isolated from 10 resistant sublines and parental HT1080 cell line. Upper panel: total RNA (20 micrograms) was electrophoreses, blotted onto a nylon membrane, and hybridized with the [$^{32}$P]dCTP-labeled human TS cDNA. Lane 1: RNA from parental HT1080 cells. Lane 2: RNA from resistant cell line HT1080-A which was selected by AG337 without EMS pretreatment. Lanes 3–11: represent 9 different resistant sublines from EMS treatment and followed by AG337 selection. Lower panel: membrane was stripped and rehybridized with a [$^{32}$P]dCTP-labeled 36B4 ribosomal control cDNA probe.

To examine whether single-step selection with relatively high AG337 concentrations after EMS pretreatment led to changes in the expression of the TS gene, cytoplasmic RNA from parental and the AG337-resistant cell line obtained without EMS exposure (HT1080/A) as well as the EMS-treated AG337-resistant cell lines with altered mobility on SSCP gels was analyzed by northern blot analysis using a human TS cDNA probe. The expression level of TS mRNA from the parental line (lane 1), and resistant cell lines (lanes 2–10) is shown in FIG. 3. Some AG337 resistant sublines (HT1080/A, HT1080/2b, HT1080/2c, HT1080/2d and HT1080/2e) have an increase in TS mRNA, but there was no increase in TS mRNA in other AG337-resistant cell lines (HT1080/1b, HT1080/1c, HT1080/1d, HT1080/1e and HT1080/6e). The results suggested that some AG337-resistant cell lines with band shifts on SSCP gels derive their resistance from a mechanism that does not appear to also involve the overexpression of TS gene.

EXAMPLE 32

Western Blot Analysis

Figure 4:
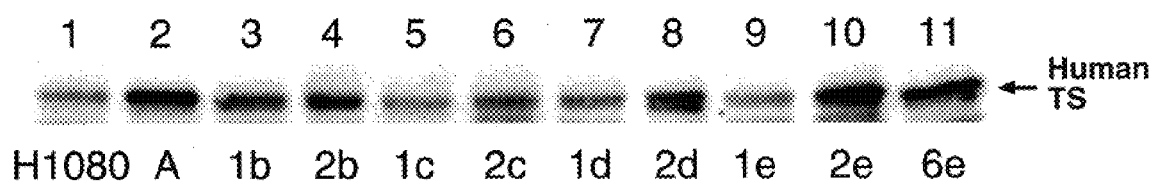
FIG. 4 shows the western blot analysis of human TS protein levels in parental HT1080 cell lines and 10 AG337-resistant cell lines. Western blot analysis for human TS was carried out using 100 micrograms of cellular lysate fractionated on 12% acrylamide gel. A rabbit antibody against human TS was used as a probe.

In order to provide further confirmation of the results obtained with Northern blot analysis which showed some AG337-resistant cell lines did not overexpress TS mRNA, expression of TS protein was measured by western blot analysis using a TS polyclonal antibody. FIG. 4 shows that by comparison with the parental HT1080 cell line, some sublines (HT1080/1b, HT1080/1c, HT1080/1d and HT1080/1e) did not exhibit detectable elevated levels of TS enzyme, and resistant sublines (HT1080/2b, HT1080/2c, HT1080/2d and HT1080/2e) expressed high levels of TS protein, being consistent with the Northern blot results. However, of interest, the subline HT1080/6e had the same mRNA level as HT1080 but overexpressed TS protein.

EXAMPLE 33

Analysis of DNA Fragments with Mobility Shifts on SSCP Gels

To elucidate the structural alterations that caused mobility shifts in fragments detected by the PCR-SSCP analysis, sequencing of these fragments was performed. Bands with mobility shifts and normal bands were present on SSCP gels. Moreover, by comparison of the aberrant bands, the normal bands had a stronger signal in general. This observation suggests that these cell lines contain both wild-type and mutant TS genes.

Direct isolation of DNA fragments from SSCP gels to perform PCR sequencing was attempted without success. It is possible that the oligonucleotides used, although, were suitable primers for PCR amplification, not useful for sequencing. DNA fragments carrying putative mutations on human TS gene were amplified and subsequently subcloned into the pCR-Script™ SK(+) vector. Several positive clones for each sample were chosen and subjected to plasmid sequencing from both directions. Over one hundred clones containing independent fragments were screened by sequence analysis. Most sequencing results were found to be identical to the wild-type human TS gene. However, twenty-five point mutations were identified and are summarized in TABLE 5 which not included five silent mutations. None of mutations was identified in parental cells even when DNA fragments were sequenced more than 10 times.

TABLE 5

Point Mutations in the TS Gene Identified by Sequence Analysis of DNA from Resistant Cell Lines

| Cell Lines | Fragments Sequenced | Point Mutation | Amino Acid Changes | Changed Amino Acid Description |
|---|---|---|---|---|
| HT1080/6e | 4A-1B | AAG→GAG | 47 Lys→Glu | Always Lys or Arg |
| HT1080/6e | 4A-1B | TAC→TGC | 65 Tyr→Cys | Always Tyr or Phe |
| HT1080/6e | 4A-1B | GTT→GCT | 84 Val→Ala | Always Val or Ile |
| HT1080/6e | 4A-1B | CGC→TGC | 50 Arg→Cys | Conserved |
| HT1080/6c | 4A-1B | GTG→ATG | 79 Val→Met | Conserved |
| HT1080/1b | 3A-3B | GCC→ACC | 228 Ala→Thr | Conserved |
| HT1080/1b | 3A-3B | CAG→CGG | 214 Gln→Arg | Conserved |
| HT1080/1b | 3A-3B | AAA→ATA | 266 Lys→Ile | Most is Lys |
| HT1080/2b | 1A-4B | GAC→AAC | 49 Asp→Asn | Conserved |
| HT1080/2b | 1A-4B | ATC→ACC | 40 Ile→Thr | Always Ile or Val |
| HT1080/1d | 1A-4B | ACG→GCG | 51 Thr→Ala | Conserved |
| HT1080/2d | 1A-4B | CGT→CAT | 25 Arg→His | Not conserved |

TABLE 5-continued

Point Mutations in the TS Gene Identified by Sequence Analysis of DNA from Resistant Cell Lines

| Cell Lines | Fragments Sequenced | Point Mutation | Amino Acid Changes | Changed Amino Acid Description |
|---|---|---|---|---|
| HT1080/2d | 1A-4B | TTC→CTC | 59 Phe→Leu | Conserved |
| HT1080/1e | 1A-4B | GGC→AGC | 52 Gly→Ser | Always Gly or His |
| HT1080/2e | 4A-1B | GAC→GGC | 49 Asp→Gly | Conserved |
| HT1080/2e | 2A-2B | GAC→GGC | 130 Asp→Gly | Conserved |
| HT1080/2e | 3A-3B | AAA→TAA | 266 Lys→Stop | Most is Lys |
| HT1080/2e | 3A-3B | ATT→ACT | 267 Ile→Thr | Not conserved |
| HT1080/2e | 3A-3B | ACG→ATG | 234 Thr→Met | Conserved |
| HT1080/2e | 3A-3B | GAT→GGT | 289 Asp→Gly | Always Asp, Glu or Phe |

Figure 5:
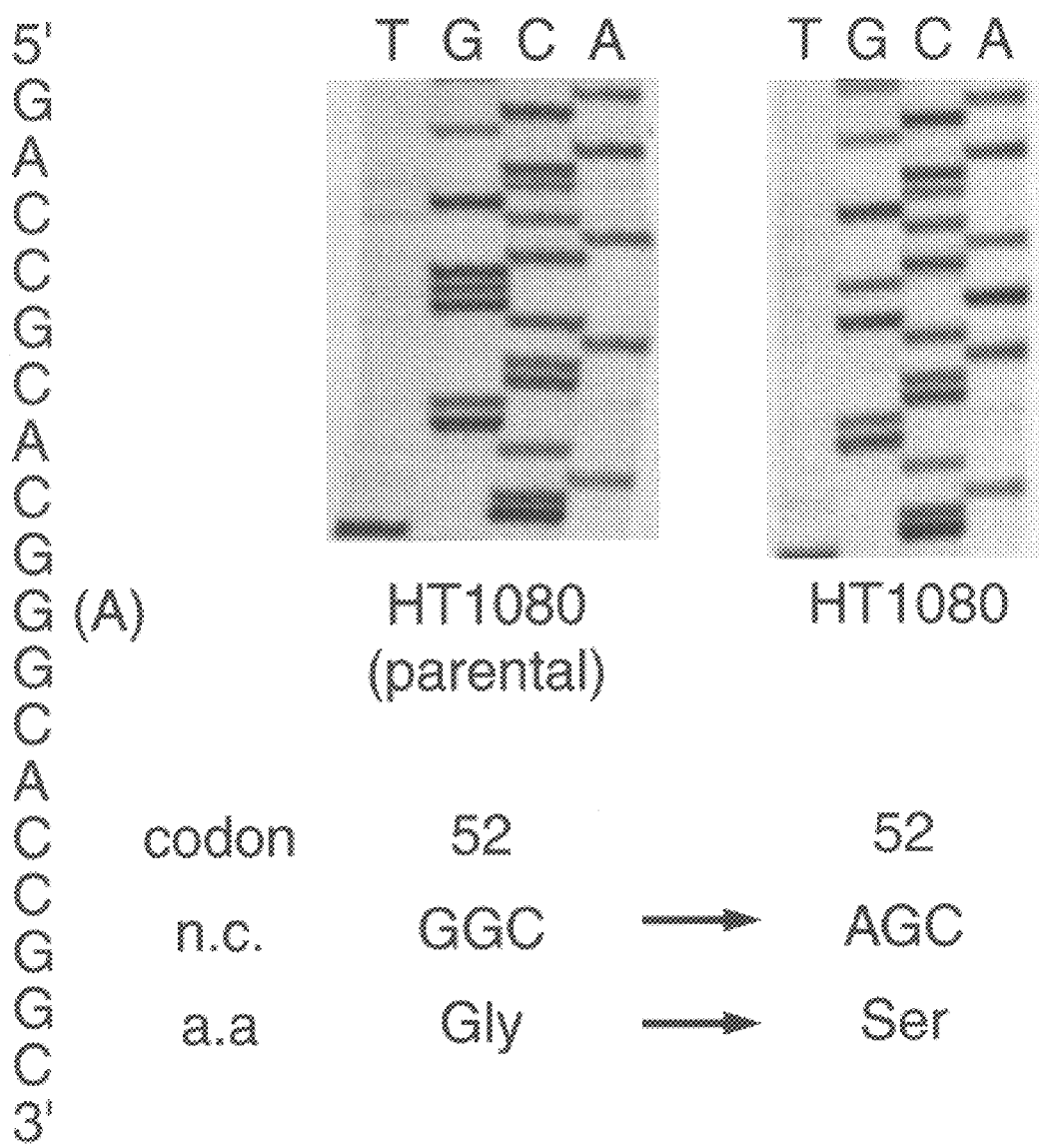
FIG. 5 shows the sequencing analysis of parental cell line HT1080 and resistant cell line HT1080/1e for human TS cDNA. The region detected between nucleotide coding 147 and 162 is shown. A point mutation occus at 154 (G→A), resulting in Ser$^{52}$ instead of Gly$^{52}$.
Figure 6:
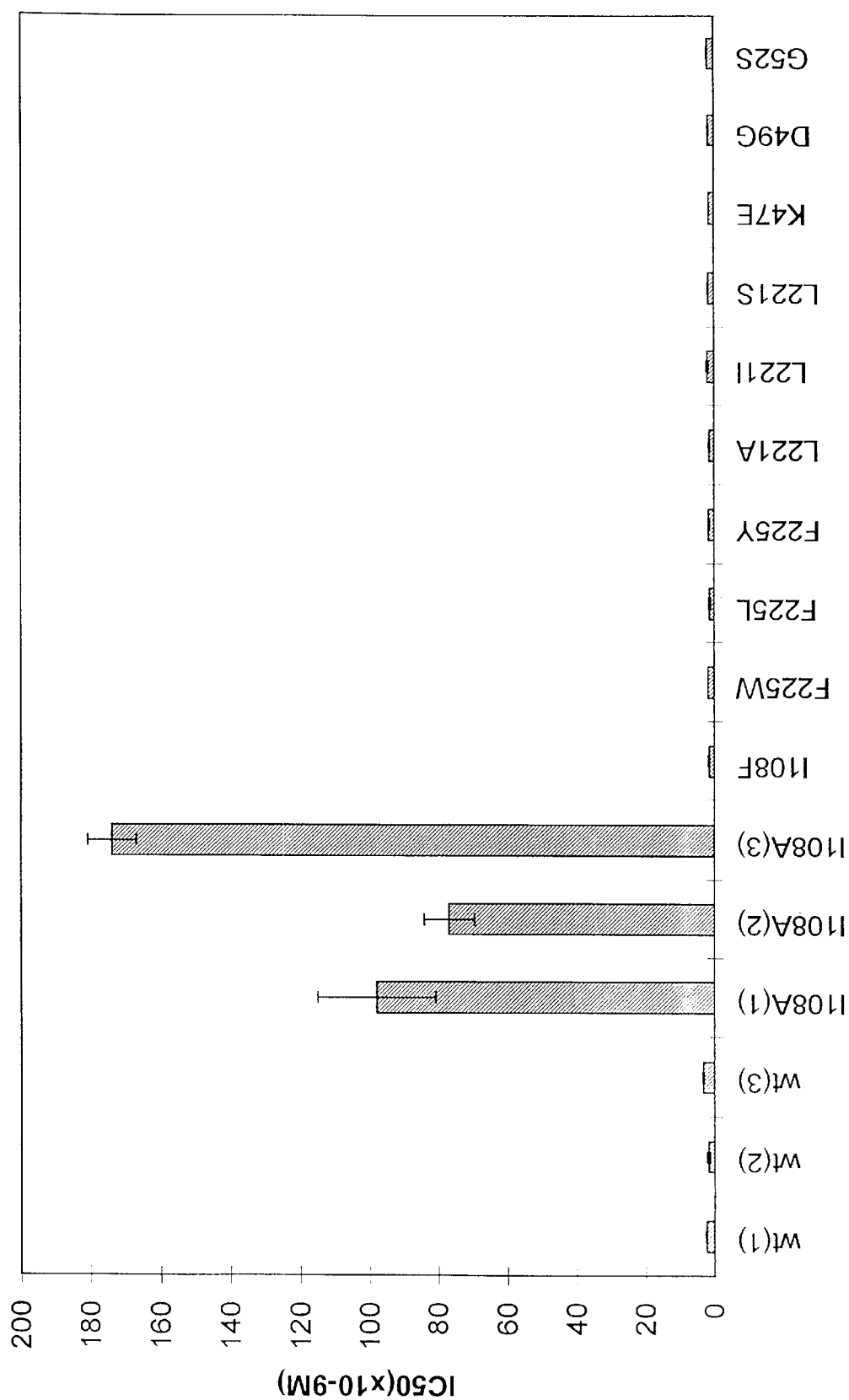
FIG. 6 shows the graphical comparison of the IC50 values for human TS mutants for tomudex (ZD1694). IC50 values were determined by Alamar Blue assay. Error bars denote the standard deviation of multiple IC50 determinations.
Figure 7:
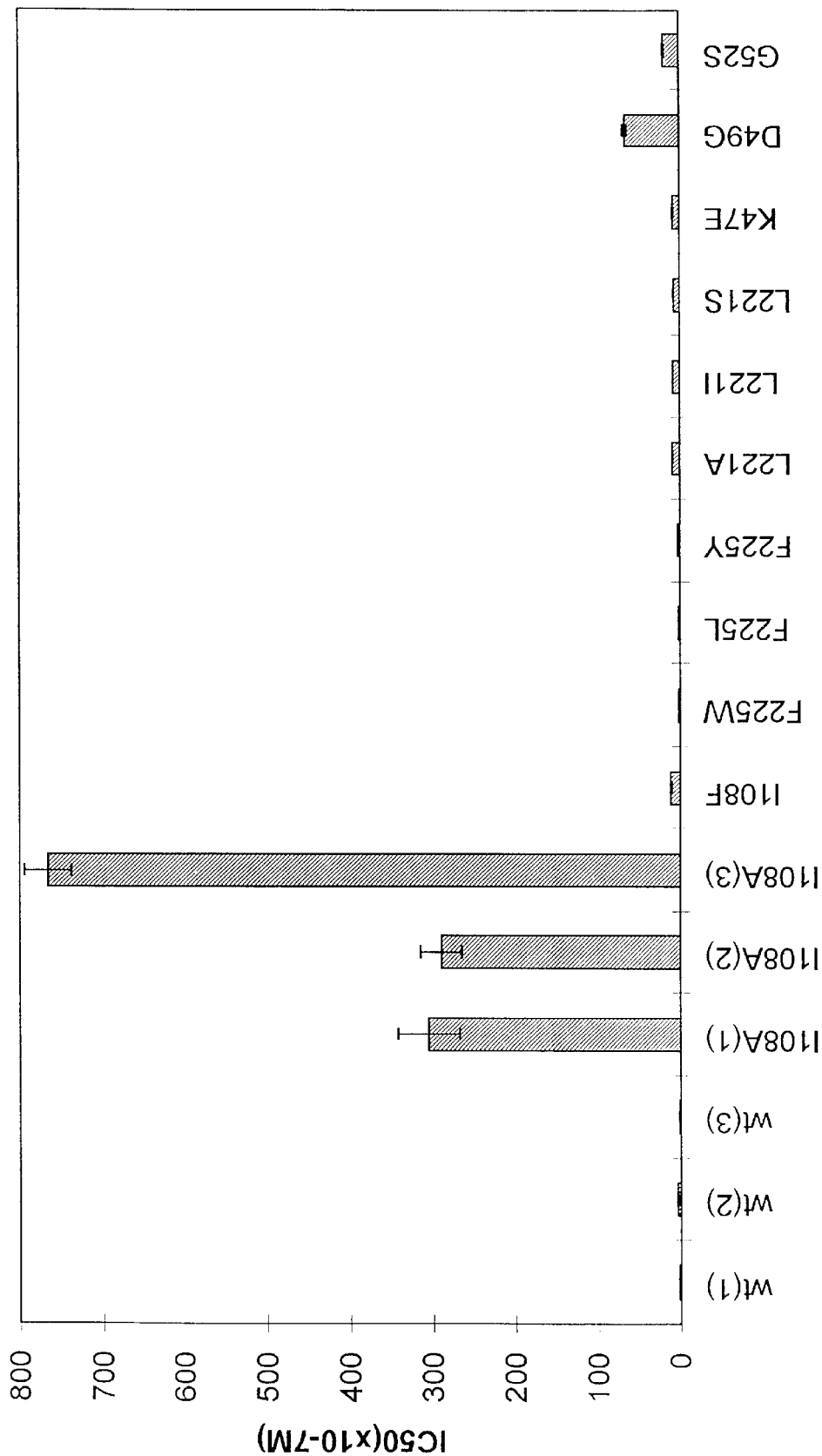
FIG. 7 shows the graphical comparison of the IC50 values for human TS mutants for AG337. IC50 values were determined by Alamar Blue assay. Error bars denote the standard deviation of multiple IC50 determinations.
Figure 8:
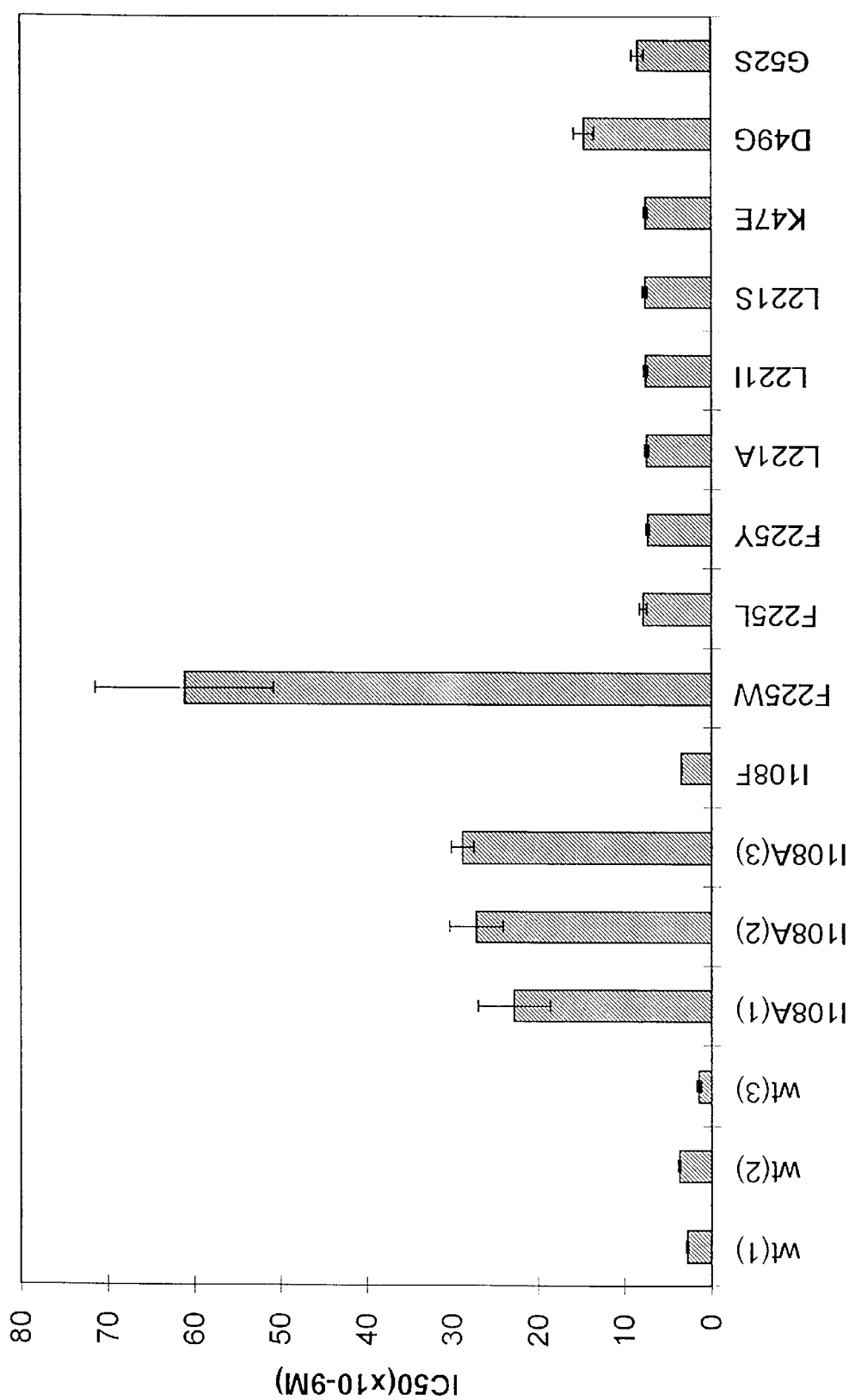
FIG. 8 shows the graphical comparison of the IC50 values for human TS mutants for BW1843U89. IC50 values were determined by Alamar Blue assay. Error bars denote the standard deviation of multiple IC50 determinations.
Figure 9:
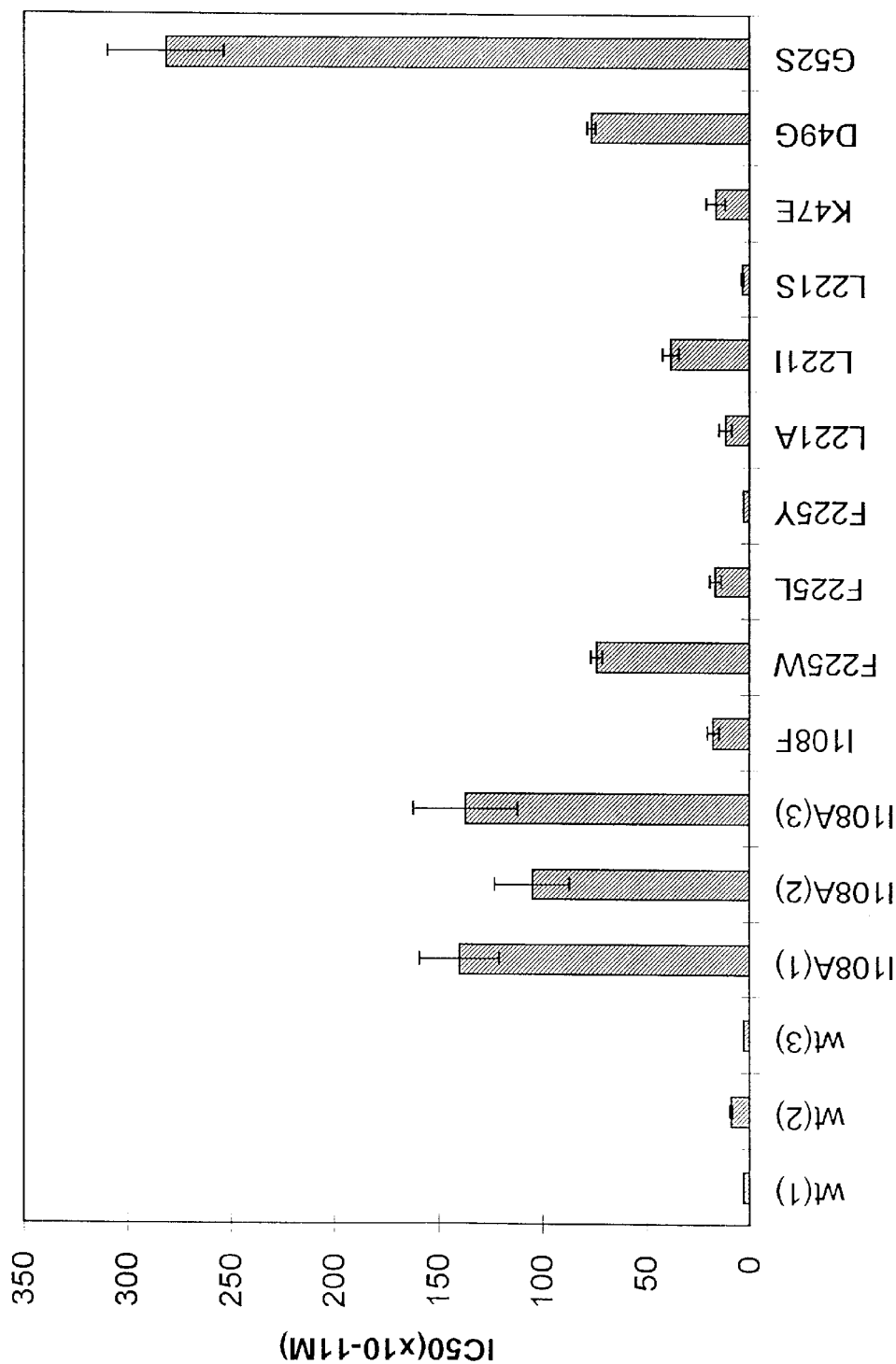
FIG. 9 shows the graphical comparison of the IC50 values for human TS mutants for FdUrd. IC50 values were determined by Alamar Blue assay. Error bars denote the standard deviation of multiple IC50 determinations.

Analysis of these nucleotide changes causing amino acid replacements revealed that 18 of 20 mutations were AT×GC or GC×AT transitions, and 2 are transversions. In addition, 18 of 20 (or 18 of 25 including the 5 silent mutations) resulted in amino acid changes in highly conserved residues. In resistant HT1080/6e cells, for example, the arginine codon (CGC) at amino acid position 50 of the TS gene is mutated to a cysteine codon (TGC) by a C to T transition. $Arg^{50}$ is a highly conserved residue which is believed to hydrogen bond with dUMP. In HT1080/1e cells, a G to A transition resulted in replacement of glycine (GGC) by serine (AGC) at amino acid residue 52 (see FIG. 5).

EXAMPLE 34

Mutagenesis of the Folate Binding Site of Human Thymidylate Synthase

Amongst the point mutations in the human TS gene of the sequence disclosed in Genbank Accession number NM001071 (SEQ ID No. 38) identified by sequence analysis from random mutagenesis studies one at position 50 is directly involved in substrate and cofactor binding. The substitutions of amino acid residues located in binding regions may cause dramatic shifts of binding affinities to substrate. Previous studies with DHFR have demonstrated that the positions 22, 31 and 34 which interact with the PABA ring of $H_2$folate are hot spots for mutagenesis and several point mutations on those sites leading to MTX resistance were found in drug resistant cell lines (Simonsen et al., 1983; Schweitzer et al., 1989). Crystal structures of TS have revealed that Ile108, Leu221 and Phe225 are residues providing hydrophobic interactions with the PABA moiety of folates when the ternary structure of TS bound nucleotide and folate is formed. None of these three residues, which all are very highly conserved, have been reported to be mutated previously in any TS species. Based on the above considerations, multiple substitutions were performed for Ile108, Leu221 and Phe225 in TS, including: (1) Trp, Ser, Leu or Tyr substitutions for Phe in position 225; (2) Phe, Arg, Ala, Ile or Ser for Leu in position 221 and (3) Ala, Phe, Gly, Glu or Asn substitutions for Ile108.

The point mutations found by EMS pretreatment and following AG337 selection include two (59 and 214) which are important for ligand binding and structural stability, and six in the Arg50 loop which becomes more ordered by movement and reorientation upon ligand binding. Therefore, those eight mutations were chosen for further analysis, using the same procedures for the mutagenesis study of the three folate binding sites. TABLE 6 shows that the mutated amino acid positions in human TS gene that are highly conserved and important in catalytic function and ligand binding.

TABLE 6

The Mutations in Human TS which are Highly Conservative for Primary Structure and Important for Ligand Binding

| Positions in human and cox L. casei thymidylate synthase | Sequence conservation among 29 TS species | Interactions with $CH_2H_4$ folate or dUMP |
|---|---|---|
| Phe225/ Phe228 | Highly conserved with one exception His | Hydrophobic contact with PABA of folate |
| Leu221/ Leu224 | Highly conserved with one exception Val | Hydrophobic contact with PABA of folate |
| Ile108/Ile81 | Highly conserved with two exceptions Val and Tyr | Hydrophobic contact with PABA of folate |
| Lys47/Lys20 | Invariant in vertebrates | Arg50 loop |
| Asp49/ Asp22 | Strictly invariant | Arg50 loop |
| Arg50/ Arg23 | Highly conserved with two exceptions Gly | Hydrogen bond with dUMP and C-terminus |
| Thr51/Thr24 | Highly conserved with one exception Gln | Arg50 loop |
| Gly52/His25 | Highly conserved with five exceptions; two His, Arg, Met & Pro | Arg50 loop |
| Phe59/Phe32 | Highly conserved with two exceptions Met and Thr | β-sheet i, forming part of the substrate binding pocket |
| Gln214/ Gln217 | Highly conserved with one exception Ala | β-sheet iii, a kick region for three β-sheet formation |

EXAMPLE 35

Construction of Mutations in Human TS

The human TS expression vector pcDNA3hTS, containing the entire coding sequence of the human TS gene of the sequence disclosed in Genbank Accession number NM001071 (SEQ ID No. 38) with minor modifications of the N-terminal nucleotide codon, was constructed. The blunt-end double-stranded fragment of human TS cDNA (950 bp) generated by digestion of the bacterial expression plasmid pET-17(bhTS with NdeI and HindIII restriction enzymes and following treatment with T4 DNA polymerase, was inserted to the unique EcoRV restriction site of vector pcDNA3. The novel constructed plasmid pcDNA3hTS under control of the T7 promoter was used to generate single strand DNA for site-directed mutagenesis and sequence analysis, as well as an mammalian expression vector. Twenty-two human TS mutants, which included 8 mutations (K47E, D49N, D49G, R50C T51A, G52S, F59L and Q214R) identified from random mutagenesis studies and another twelve multiple replacements of Ile108, Leu221 and Phe225 were prepared by site-directed mutagenesis using pcDNA3hTS as a template, following the instructions described by the Transformer™ site-directed mutagenesis kit (2nd version, Clontech). The selective primer was designed to change the unique restriction site SmaI to KspI and twenty-two mutagenic primers with 1 to 3 nucleotide changes were optimized with a computer program for oligo design. Sequencing the coding regions demonstrated that the expected substitution had been introduced and that no other alteration had occurred (data not shown). TABLE 9 lists the site of the mutations obtained in the eukaryotic expression plasmids.

EXAMPLE 37

Growth Sensitivity to Antifolates and FdUrd

Before determining growth sensitivity to three antifolates (tomudex, AG337, and BW1843U89) and 5-fluoro-2'-deoxyuridine (FdUrd), the levels of human TS protein for the transfectants were demonstrated by western blot analyses. Two I108A mutant clones (175-1 and 175-2) expressed levels of TS protein at the same level as that of a control clone (161-2) transfected with the wild-type vector (TABLE 8-11). Using the TS protein level expressed by the above three cell clones as a standard, cell clone 175-3 had slightly higher and clones 161-1 and 161-2 had lower levels of protein. For the other 10 transfectants with human TS variants, cell clones expressing similar TS levels as the standard were chosen.

TABLE 7

Eukaryotic Expression Plasmids Containing Mutants of Human TS and the Results of Rescue Experiments Mouse TS-Negative Cells

| a.a number | Point mutation | a.a change | Reason for change | Eukaryotic expression | Protein expression system | FM3A TS cells surviving by transfection | Reference number |
|---|---|---|---|---|---|---|---|
| wt | | | | pcDNA3hTS161* | pET-17xbhTS161 | yes | 161 |
| 225 | TTC→TGG | Phe→Trp | S. information | pcDNA3hTS162 | pET-17xbhTS162 | yes | 162 |
| 225 | TTC→TCC | Phe→Ser | S. information | pcDNA3hTS163 | | no | 163 |
| 225 | TTC→CTC | Phe→Leu | S. information | pcDNA3hTS83 | | yes | 83 |
| 225 | TTC→GCC | Phe→Tyr | S. information | pcDNA3hTS84 | | yes | 84 |
| 221 | CTC→TTC | Leu→Phe | S. information | pcDNA3hTS164 | | no | 164 |
| 221 | CTC→CGC | Leu→Arg | S. information | pcDNA3hTS165 | | no | 165 |
| 221 | CTC→GCC | Leu→Ala | S. information | pcDNA3hTS85 | | yes | 85 |
| 221 | CTC→ATC | Leu→Ile | S. information | pcDNA3hTS86 | | yes | 86 |
| 221 | CTC→AGC | Leu→Ser | S. information | pcDNA3hTS87 | | yes | 87 |
| 108 | ATC→GGC | Ile→Ala | S. information | pcDNA3hTS175 | pET-17xbhTS175 | yes | 175 |
| 108 | ATC→TTC | Ile→Phe | S. information | pcDNA3hTS176 | | yes | 176 |
| 108 | ATC→GGC | Ile→Gly | S. information | pcDNA3hTS270 | | no | 270 |
| 108 | ATC→GAG | Ile→Glu | S. information | pcDNA3hTS271 | | no | 271 |
| 108 | ATC→AAC | Ile→Asn | S. information | pcDNA3hTS272 | | no | 272 |
| 47 | AAG→GAG | Lys→Glu | EMS treatment | pcDNA3hTS925 | | yes | 925 |
| 49 | GAC→AAC | Asp→Asn | EMS treatment | pcDNA3hTS923 | | no | 923 |
| 49 | GAC→GGC | Asp→Gly | EMS treatment | pcDNA3hTS928 | pET-17xbhTS928 | yes | 928 |
| 50 | CGC→TGC | Arg→Cys | EMS treatment | pcDNA3hTS926 | | no | 926 |
| 51 | ACG→GCG | Thr→Ala | EMS treatment | pcDNA3hTS924 | | no | 924 |
| 52 | GGC→AGC | Gly→Ser | EMS treatment | pcDNA3hTS927 | pET-17xbhTS927 | yes | 927 |
| 59 | TTC→CTC | Phe→Leu | EMS treatment | pcDNA3hTS75 | | no | 75 |
| 214 | CAG→CGG | Gln→Arg | EMS treatment | pcDNA3hTS76 | | no | 76 |

*the number indicates different mutations and is consistent with reference number.

EXAMPLE 36

Rescue of TS-negative Cells by Transfection of Human TS cDNA's

The stable transfection of human TS variants into a TS-negative mouse cell was used to demonstrate whether or not the altered TS protein had enough catalytic activity for allowing normal growth in the absence of thymidine. Mouse TS-negative cells (FSthy21) were transfected with a plasmid (pcDNA3hTS*) encoding wild-type or a various mutant human TS enzyme by standard DOTAP transfection procedures. The host cells are deficient in TS, which are unable to survive without exogenous thymidine. The results of the rescue experiment showed that 11 transfectants of TS variants (I108A, I108F, F225W, F225L, F225Y, L221A, L221I, L221S, K47E, D49G, and G52S) as well as wild-type TS were able to complement growth of TS-negative cells in selective medium lacking thymidine (TABLE 7). In contrast, cells were unable to survive with transfection of other 11 human TS variants. For each surviving transfectant, at least 12 individual clones were isolated by soft agar or limiting dilution in 96-well plates. Those clones were expanded to cell lines by growth in normal media. Three cell clones for each transfectant were randomly selected for drug sensitivity assay.

The effect of three antifolates and FdUrd on the growth characteristics of transfectants that stably express various TS proteins was evaluated by cytotoxicity studies. Cell growth was measured by the alamar blue assay. $IC_{50}$ values were calculated as the concentration of inhibitor required to inhibit growth by 50% compared to wild-type transfected cells grown under identical conditions. For various transfectants, the $IC_{50}$ values of antifolates (AG337, tomudex, and BW1843U89) and FdUrd are presented in TABLES 8–11, and the graphical comparisons of the $IC_{50}$ values are given in FIGS. 6–9. As indicated, statistically significant differences in the $IC_{50}$ values were obtained: (1) I108A transfectants display resistance to tomudex and AG337 with $IC_{50}$ values at least 43- and 76-fold greater than wild-type transfectants, respectively; (2) D49G and G52S transfectants confer resistance to AG337 (40- and 12-fold respectively); (3) F225W transfectants are 22-fold resistant to BW1843U89; (4) G52S, D49G and F225W mutants demonstrate FdUrd 97-, 26-, and 25-fold resistance.

TABLE 8

Tomudex (ZD1694) Sensitivity in TS-negative Cells Transfected by Wild Type and Various Mutant Human TS cDNA's

| Transfected TS-negative cells and its clone | $IC_{50}$ values ($\times 10^{-9}$ M)[1] | Ratio of $IC_{50}$ values for mutant/wt cells | Reference number |
|---|---|---|---|
| wild-type/clone (1) | 2.37 ± 0.18 | | 161-1 |
| wild-type/clone (2) | 1.80 ± 0.47 | | 161-2 |
| wild-type/clone (3) | 3.37 ± 0.34 | | 161-3 |
| I108A/clone (1) | 97.9 ± 17.1 | 54(2)[2] | 175-1 |
| I108A/clone (2) | 76.8 ± 7.3 | 43(2) | 175-2 |
| I108A/clone (3) | 174 ± 7 | 97(2) | 175-3 |
| I108F/clone (2) | 1.52 ± 0.20 | 0.84(2) | 176-2 |
| F225W/clone (2) | 1.76 ± 0.01 | 0.98(2) | 162-2 |
| F225L/clone (3) | 1.33 ± 0.29 | 0.74(2) | 83-3 |
| F225Y/clone (1) | 1.53 ± 0.17 | 0.85(2) | 84-1 |
| L221A/clone (2) | 1.46 ± 0.09 | 0.81(2) | 85-2 |
| L221I/clone (1) | 1.98 ± 0.40 | 1.1(2) | 86-1 |
| L221S/clone (2) | 1.80 ± 0.06 | 1.0(2) | 87-2 |
| K47E/clone (2) | 1.53 ± 0.04 | 0.85(2) | 925-2 |
| D49G/clone (1) | 1.76 ± 0.09 | 0.98(2) | 928-1 |
| G52S/clone (3) | 1.94 ± 0.05 | 1.1(2) | 927-3 |

[1]$IC_{50}$ values were obtained following 7-day exposures from full dose-response curves and represent the mean ± SE (standard error) of at least 2 separate experiments involving duplicate samples from replicate cultures.
[2]The number in parentheses indicated which clone of wild-type TS transfected cells was compared.

TABLE 9

AG337 Sensitivity Expressed in TS-negative Cells Transfected by Wild Type and Various Mutant Human TS cDNA's

| Transfected TS-negative cells and its clone | $IC_{50}$ values ($\times 10^{-7}$ M)[1] | Ratio of $IC_{50}$ values for mutant/wt cells | Reference number |
|---|---|---|---|
| wild-type/clone (1) | 1.64 ± 0.08 | | 161-1 |
| wild-type/clone (2) | 3.83 ± 0.69 | | 161-2 |
| wild-type/clone (3) | 1.49 ± 0.21 | | 161-3 |
| I108A/clone (1) | 305 ± 37 | 80(2)[2] | 175-1 |
| I108A/clone (2) | 290 ± 25 | 76(2) | 175-2 |
| I108A/clone (3) | 766 ± 28 | 200(2) | 175-3 |
| I108F/clone (2) | 11.4 ± 1.2 | 7.0(2) | 176-2 |
| F225W/clone (2) | 0.70 ± 0.35 | 1.0(1) | 162-2 |
| F225L/clone (3) | 1.64 ± 0.56 | 1.0(1) | 83-3 |
| F225Y/clone (1) | 2.38 ± 0.45 | 1.5(1) | 84-1 |
| L221A/clone (2) | 8.96 ± 0.34 | 5.5(1) | 85-2 |
| L221I/clone (1) | 8.51 ± 0.18 | 5.2(1) | 86-1 |
| L221S/clone (2) | 7.38 ± 0.28 | 4.5(1) | 87-2 |
| K47E/clone (2) | 8.25 ± 0.61 | 5.0(1) | 925-2 |
| D49G/clone (1) | 66.7 ± 2.5 | 40(1) | 928-1 |
| G52S/clone (3) | 19.1 ± 0.71 | 12(1) | 927-3 |

[1]$IC_{50}$ values were obtained following 7-day exposures from full dose-response curves and represent the mean ± SE (standard error) of at least 2 separate experiments involving duplicate samples from replicate cultures.
[2]The number in parentheses indicated which clone of wild-type TS transfected cells was compared.

TABLE 10

BW1843U89 Sensitivity in TS-negative Cells Transfected by Wild Type and Various Mutant Human TS cDNA's

| Transfected TS-negative cells and its clone | $IC_{50}$ values ($\times 10^{-9}$ M)[1] | Ratio of $IC_{50}$ values for mutant/wt cells | Reference number |
|---|---|---|---|
| wild-type/clone (1) | 2.78 ± 0.12 | | 161-1 |
| wild-type/clone (2) | 3.68 ± 0.14 | | 161-2 |
| wild-type/clone (3) | 1.44 ± 0.28 | | 161-3 |
| I108A/clone (1) | 22.8 ± 4.2 | 6.2(2)[2] | 175-1 |
| I108A/clone (2) | 27.2 ± 3.1 | 7.4(2) | 175-2 |
| I108A/clone (3) | 28.8 ± 1.3 | 7.8(2) | 175-3 |
| I108F/clone (2) | 3.44 ± 0.03 | 1.2(1) | 176-2 |
| F225W/clone (2) | 61.1 ± 10.3 | 22(1) | 162-2 |
| F225L/clone (3) | 7.84 ± 0.44 | 2.8(1) | 83-3 |
| F225Y/clone (1) | 7.32 ± 0.17 | 2.6(1) | 84-1 |
| L221A/clone (2) | 7.41 ± 0.25 | 2.7(1) | 85-2 |
| L221I/clone (1) | 7.53 ± 0.25 | 2.7(1) | 86-1 |
| L221S/clone (2) | 7.63 ± 0.26 | 2.7(1) | 87-2 |
| K47E/clone (2) | 7.55 ± 0.23 | 2.7(1) | 925-2 |
| D49G/clone (1) | 14.7 ± 1.2 | 5.3(1) | 928-1 |
| G52S/clone (3) | 8.4 ± 0.7 | 3.0(1) | 927-3 |

[1]$IC_{50}$ values were obtained following 7-day exposures from full dose-response curves and represent the mean ± SE (standard error) of at least 2 separate experiments involving duplicate samples from replicate cultures.
[2]The number in parentheses indicated which clone of wild-type TS transfected cells was compared.

TABLE 11

5-Fluoro-2'-deoxyuridine (FdUrd) Sensitivity in TS-negative Cells Transfected by Wild Type and Various Mutant Human TS cDNA's

| Transfected TS-negative cells and its clone | $IC_{50}$ values ($\times 10^{-11}$ M)[1] | Ratio of $IC_{50}$ values for mutant/wt cells | Reference number |
|---|---|---|---|
| wild-type/clone (1) | 2.90 ± 0.03 | | 161-1 |
| wild-type/clone (2) | 8.96 ± 0.62 | | 161-2 |
| wild-type/clone (3) | 2.86 ± 0.02 | | 161-3 |
| I108A/clone (1) | 140 ± 19 | 16(2)[2] | 175-1 |
| I108A/clone (2) | 105 ± 18 | 12(2) | 175-2 |
| I108A/clone (3) | 137 ± 25 | 15(2) | 175-3 |
| I108F/clone (2) | 17.6 ± 2.8 | 6.1(1) | 176-2 |
| F225W/clone (2) | 73.8 ± 2.6 | 25(1) | 162-2 |
| F225L/clone (3) | 16.5 ± 2.8 | 5.7(1) | 83-3 |
| F225Y/clone (1) | 3.01 ± 0.06 | 1.0(1) | 84-1 |
| L221A/clone (2) | 11.6 ± 3.1 | 4.0(1) | 85-2 |
| L221I/clone (1) | 38.1 ± 4.1 | 13(1) | 86-1 |
| L221S/clone (2) | 3.49 ± 0.55 | 1.2(1) | 87-2 |
| K47E/clone (2) | 16.4 ± 4.5 | 5.7(1) | 925-2 |
| D49G/clone (1) | 76.3 ± 1.9 | 26(1) | 928-1 |
| G52S/clone (3) | 282 ± 28 | 97(1) | 927-3 |

[1]$IC_{50}$ values were obtained following 7-day exposures from full dose-response curves and represent the mean ± SE (standard error) of at least 2 separate experiments involving duplicate samples from replicate cultures.
[2]The number in parentheses indicated which clone of wild-type TS transfected cells was compared.

To determining if different expressed TS levels in transfectants contributed to drug sensitivity changes of the $IC_{50}$ values of four drugs, multiple clones of wild-type and I108A mutant transfections were compared to TS levels. Clone 175-3, having the highest TS levels, is more resistant to tomudex and AG337 than clone 175-1 and 175-2 but there was no marked increase in $IC_{50}$ values to BW1843U89 and FdUrd. The biggest difference in $IC_{50}$ values between clones 175-2 and 175-3 for AG337 was less than 3-fold. Similar results with relatively less changes of drug sensitivity were also obtained using three individual clones of wild-type transfectants. These data suggested that the changes in drug sensitivity by different clones transfected with the same vector are roughly proportional to their expressed protein levels. However, the major reason causing dramatic changes in $IC_{50}$ values was due to expression of TS variants and the levels of TS protein was less important.

EXAMPLE 38

Subcloning and Expression of Human TS in *E. coli*

Based on the drug sensitivity results presented, human TS mutations I108A (175), F225W (162), D49G (928) and G52

(927) were selected for enzyme kinetic studies. The fragments encompassing the entire human TS cDNA with different mutations, amplified by a pair of designed primers that contained NdeI and XhoI restriction sites in the 5' and 3' primers respectively, were subcloned into the pET-17xb vector utilizing corresponding NdeI and XhoI sites. The pET system was developed to provide the high yields of soluble protein in *E. coli*. These protein expression vectors were designated as pET-17xbhTS175, pET-17xbhTS162, pET-17xbhTS928, and pET-17xbhTS927 (see Table 7). The expression of wild-type and mutant TSs was carried in a derivative of the *E. coli* strain BL21 after IPTG induction. The activity of the enzyme was monitored and found to be highest at 4–5 h after the addition of IPTG. In the absence of IPTG the activity from extracts of transformed BL21 cells was much lower and probably represents background *E. coli* TS activity. *E. coli* extracts after 4–5 h of IPTG induction were analyzed by SDS-PAGE and revealed an intensely staining band at a molecular mass of about 36 kDa, absent from extracts of the host *E. coli* cells. This new protein band was estimated to represent about 10–20% of the total soluble protein in the extract. The crude extracts from bacteria cells transformed by mutant TS vectors had similar high levels of production of the altered proteins.

EXAMPLE 39

Purification of Mutant TS Proteins

A purification procedure using sequential ion exchanger/phenyl-sepharose chromatography was adopted for purifying wild-type and mutant human TS proteins (Ciesla et al., 1995). The procedure of Ciesla et al. was modified in that the human TS was eluted from phenyl-sepharose using a linear gradient of ammonium sulfate of 0.6 M to 0 instead of 0.8 to 0.4 M employed for rat proteins. After purification, a single major component on SDS-PAGE gel migrating with an apparent molecular weight of human TS protein was observed for all mutant enzymes. Purity was estimated to be higher than 90% as determined by densitometric scanning.

EXAMPLE 40

Kinetic Properties of Mutant Enzymes

In order to obtain more detailed information about the catalytic and ligand-binding properties of these TS variants, kinetic parameters such as $V_{max}$ and $K_m$'s for substrate and cofactor, and $K_i$'s for inhibitors were evaluated. The results for wild-type and mutant TSs are presented in TABLE 12.

The Michaelis constant ($K_m$) values for dUMP was not significantly different between the wild-type and F225W mutant forms while the catalytic efficiency ($k_{cat}$) of F225W was even higher than the $k_{cat}$ of wild-type TS. However, $K_m$ values for $CH_2H_4$folate differed markedly with a 4-fold increase for F225W mutant over wild-type. More dramatic changes were noted with the I108A mutant. Its affinity for cofactor was decreased to a much larger degrees (22-fold) than for dUMP (4-fold). The $K_m$ for $CH_2H_4$folate and dUMP of the D49G variant was increased 4-fold over wild-type TS. Both I108A and D49G mutants showed diminished catalytic activity with $k_{cat}$ values 3-fold lower than wild-type TS.

TABLE 12

Kinetic Parameters for Wild-Type and Mutant Human Thymidylate Synthases

| Enzyme | $K_m$ ($CH_2H_4$folate) (µM) | $K_m$ (dUMP) (µM) | $k_{cat}$ (sec$^{-1}$) | Reference #[b] |
|---|---|---|---|---|
| wt | 32.4 | 4.4 | 0.68 | 161 |
| F225W | 165 | 3.6 | 2.3 | 162 |
| I108A | 746 | 15 | 0.22 | 175 |
| G52S | ND[a] | ND | ND | 927 |
| D49G | 122 | 12 | 0.16 | 928 |

[a] not determined,
[b] refers to Table 7.

TABLE 13

Binding affinity of Tomudex, AG337, BW1843U89 and FdUMP for Wild-Type and Mutant Human Thymidylate Synthase

| Inhibition Constants ($K_i$ (nM)) | wt | Variants of TS | | | |
| | | I108A | F225W | G52S | D49G |
|---|---|---|---|---|---|
| Tomudex | 7.0 | 4100 | 87 | ND* | 53 |
| Variant/wt | — | 580 | 13 | ND | 7.6 |
| BW1843U89 | 0.09[b] | 2400 | 23 | ND | 180 |
| Variant/wt | | 27000[c] | 260 | ND | 2000 |
| AG337 | 16 | 1400 | 5.3 | ND | 130 |
| Variant/wt | | 91 | 0.35 | ND | 8.1 |
| FdUMP | 11 | 22 | 25 | ND | 23 |
| Variant/wt | | 2.0 | 2.3 | ND | 2.1 |
| Reference #[d] | 161 | 175 | 162 | 927 | 928 |

[a] not determined;
[b] obtained from previous report;
[c] by comparison with previous data;
[d] refers to Table 7

EXAMPLE 41

Transfection of Wild Type (TS161) and Mutant (TS175) Plasmid

DNA into Mouse Bone Marrow Progenitor Cells Twenty micrograms of plasmid DNA (TS161 or TS175) and ten micrograms of DOTAP were diluted to 100 µl with HBS buffer and incubated at room temperature for 10 minutes. The mixture was added to 2×10⁶ mouse bone marrow cells suspended in 0.5 ml of IMDM medium (in a 35 mm culture dish). After a 4 hour incubation at 37° C., 2 ml of IMDM with 30% FBS was added to each dish and the incubation was continued for 24 hours. At this time, another 4 ml of fresh medium with 10% FBS was added to each dish and incubation continued for an additional 48 hours.

Transfected cells prepared as described above were distributed into 10×35 mm dishes (3×10⁵ cells in 6 ml IMDM media/dish). The media contained 1% methyl cellulose, 20% FBS, 10% WEHI-3B conditioned media, 1% sodium pyruvate, 1 mM mercaptoethanol, 100 µg/ml of penicillin, 100 µg/ml streptomycin, 1% essential amino acids, 1.5% nonessential amino acids and 0.5% ascorbate. Drug was added at the indicated concentration to each dish and the cells were cultured at 37° C. (5% $CO_2$) for 10–14 days. CFU-GM colonies (>50 cells) were counted and larger colonies (>1000 cells) HPPCFU-C (high proliferation colony forming cells) were counted under the microscope. TABLE 14 shows that mouse marrow CFU-CM colonies and HPPCFU colonies transfected with a plasmid containing the mutant TS (TS175) had greater resistance to tomudex (D1694) and AG337 than mouse marrow CFU-CM colonies and HPPCFU colonies transfected with a plasmid containing the wild type TS (TS161).

TABLE 14

Resistance to tomudex (D1694) and AG337 in mouse marrow CFU-CM colonies and HPPCFU colonies after transfection with plasmids containing wild type TS (TS161) and mutant TS (TS175)

| | CFU-GM Assay | | | | |
|---|---|---|---|---|---|
| | | tomudex | | AG337 | |
| | 0 | $2 \times 10^{-8}$ M | $1 \times 10^{-8}$ M | $2 \times 10^{-7}$ M | $1 \times 10^{-8}$ M |
| N.B.M. | 2 | 0 | 14(17%) | 0 | 10(12%) |
| TS161 | 108 | 0 | 28(26%) | 0 | 20(19%) |
| TS175 | 144 | 14(10%) | 64(44%) | 12(8%) | 60(42%) |

| | HPPCFU-C Assay | |
|---|---|---|
| | tomudex $1 \times 10^{-8}$ M | AG337 $1 \times 10^{-7}$ M |
| N.B.M. | 0 | 0 |
| TS161 | 0 | 0 |
| TS175 | 9(6%) | 8(6%) |

Discussion

Several point mutations in *E. coli* and *L. casei* TS gene were previously made by cassette and site-directed mutagenesis. The procedures included two steps; generated mutants were first screened for their catalytic activity by complementing the growth of TS-negative *E. coli* cells in the absence of thymine and kinetic characterizations were subsequently performed for functional mutants. Alternative approaches were adopted for the studies focusing on human TS mutants. Firstly, random mutagenesis were performed by exposure of human sarcoma HT1080 cells to an alkylating agent (EMS) and selection with AG337, to generate putative mutations leading to AG337 resistance. These isolated mutants were utilized to measure their binding to other TS inhibitors such as tomudex, BW1843U89 and FdUrd. Moreover, mutations made by EMS could occur anywhere in the entire TS gene and were not limited to specific gene regions as in cassette mutagenesis. However, as it is almost impossible to obtain double or triple point mutations in a nucleotide codon by random mutagenesis, therefore some desirable amino acid substitutions are excluded by this approach. The functional roles of individual amino acid residues were examined, especially their effects on the binding of the folate cofactor or inhibitors by generating specific mutations. Fourteen mutations at positions 108, 221 and 225 that are involved in hydrophobic interactions of TS with cofactor or inhibitors were created by site-directed mutagenesis. The target residues were chosen because they are highly conserved and because they are important for folate binding as indicated by X-ray crystallographic studies. In addition, multiple substitution studies for these three amino acid residues have not yet been reported on all species of TS. Mouse TS-deficient cells instead of TS-negative *E. coli* cells were used as a host for expression of mutant TS enzymes, which allowed an assessment of catalytic activity and provided a mammalian test system for evaluating the effects of inhibitors of TS.

The present invention obtained human TS variants that conferred resistance to novel antifolates, with a minimal changes in the catalytic activity of the enzyme. Such variants are of interest for several reasons, particularly for their use in gene therapy to protect hemotopoietic progenitors from drugs, such as tomudex. The results described herein demonstrate that several human TS mutants have desirable properties that support their use in such gene therapy studies. The present invention obtained information on the mode of binding of $CH_2H_4$folate and inhibitors to TS indicating that the different TS inhibitors bind to TS in different ways.

Human TS Mutants Identified in EMS-Exposed Cells

Single-stranded conformation polymorphism (SSCP) is a simple and sensitive approach to analyze nucleotide changes which result in altered mobility of DNA fragments on non-denaturing polyacrylamide gels. However, SSCP sensitivity varies dramatically with the size of the DNA fragment. The optimal size of DNA fragments are approximately 150 bp in length. When the presence of point mutations in EMS-exposed AG337-resistant cells was investigated by SSCP analysis, 6-pairs of primers were used to span the cDNA for TS, each amplified 150–260 bp fragments. By screening of almost the entire coding sequence of human TS gene from AG337-resistant HT1080 sublines, shifted bands in addition to normal migrating bands were observed on SSCP gels, indicating the presence of wild-type and mutant TS genes in the sample. Polymorphisms can be detected when mutant DNA comprised as little as 3% of the total gene copies in a PCR mixture (Hongyo et al., 1993). However, SSCP cannot discriminate between pre-existing mutations and those mutations introduced by Taq polymerase errors during amplification.

After EMS exposure, a relatively large number of drug resistant clones could be obtained by selection with TMTX, a lipophilic DHFR inhibitor. An increase in frequency of drug resistant clones was also observed in the mutagenesis experiment using AG337 as a selective drug. Unexpectedly, more than 20 mutations of human TS were identified in AG337-resistant sublines. In order to explain the large number of mutations, it was postulated that EMS exposure and Taq polymerase errors contributed to the point mutations found after SSCP and sequence analysis. Other less likely possibilities that would cause mutations include selection with AG337 which could act as a weak mutagen, and infidelity of AMV reverse transcriptase.

For mutations caused by EMS exposure as well as Taq polymerase errors, transitions are more likely to predominant over transversions. For Taq polymerase, the most common transition was AT×GC (72% of all changes), and the remaining base substitutions were observed at roughly equivalent frequencies (Tindall et al., 1988). However, in contrast to infidelity of Taq polymerase, EMS-induced GC×AT transitions were much more common than AT×GC transitions (65% of all).

Based on above information, if all or most of the mutations identified in EMS-exposed cells were caused by Taq polymerase error, AT×GC transitions should be dominant. Otherwise, some mutations could be generated by EMS exposure. The mutation results showed that AT×GC and GC×AT transitions were roughly equal (see TABLE 6), indicating that some or most of those mutations were generated by EMS exposure. This conclusion is supported by evidence that none of the mutations were detected in controls, in which parent HT1080 cells without EMS and AG337 exposure were tested. Most amino acid substitutions were found in highly conserved positions, suggesting that these variants were likely to lead to drug resistance. Therefore, 8 mutations were selected for studies in mouse TS-negative cells for directly examining the ability of these mutations to allow growth in the absence of thymidine. Cytotoxicity studies showed that D49G and G52S TS variants display resistance to the selective drug AG337, providing additional proof that these mutations were involved in the AG337 resistant phenotype selection.

The Arg50 Loop and Drug Resistance

Surprisingly, of the 20 point mutations identified from the random mutagenesis, six occurred in the highly conserved Arg50 loop. This loop connects elements of protein secondary structure, an α-helix A (residues 30–43) near the N-terminus and a β-sheet i (residues 54–66) (Montfort et al., 1990). When Agouron designed folate analogues such as AG337, the quinazoline ring system was kept intact, based on observations from the humanized $E.$ $coli$ TS model (Reich et al., 1992). Hydrogen-bonding was predicted to occur between the carboxylate of Asp218 and hydrogen on N-3 of quinazoline ring, and another between N-1 of quinazoline ring and a fixed $H_2O$ molecule which in turn is hydrogen bonded to Val313 and Arg50. Therefore, Arg50 is believed to play a in the structure-based drug design. Moreover, in the native unbound TS, the Arg50 loop is mobile. Once the ternary complex is formed, the carboxylate of the C-terminal residue forms a hydrogen bond network with Arg50, which shifts 0.5 Å to interact with the phosphate of dUMP and hydrogen-bond with N-1 of $CH_2H_4$folate via $H_2O$. This flexible residue Arg50 seems to be a bridge to link the enzyme C-terminus, substrate and cofactor (or antifolates) together. The movement of the Arg50 residue is accompanied by adjustment and reorientation of its neighbor residues, indicating that the entire Arg50 loop undergoes relocation and experiences new interactions. For example, the hydrophobic atoms of Thr51 has contacts with the buried Val313 side chain after movement. Besides structure studies, the residues in Arg50 loop have been studied by mutagenesis of $E.$ $coli$ and $L.$ $casei$ TS. The present invention indicates that the modification of the loop Arg50 causes changes on binding affinity leading to drug resistance, which is related to not only folate but also nucleotides.

Arg50 is extremely sensitive to substitution by other amino acids, as shown with both $L.$ $casei$ and $E.$ $coli$ TS. The R50C mutant of human TS is catalytically inactive, and the T51A and D49N mutants are also not tolerated, which is consistent with comparably altered $L.$ $casei$ and $E.$ $coli$ TS. However, 3 other point mutations (K47E, D49G and G52S) retain TS catalytic function. Cytotoxicity assays also showed that expressed D49S and G52S mutant protein in mouse TS-negative cells confers resistance to AG337 with $IC_{50}$ values 40- and 12-fold greater than cells expressing wild-type TS expressed cells respectively. These mutant transfected cell lines also display resistance to FdUrd (26- and 97-fold respectively) but not to tomudex or BW1843U89. The $K_m$ values for $CH_2H_4$folate and dUMP of the D49S mutant protein also demonstrated that the mutation equally affects both the substrate and cofactor binding with about a 4-fold increase in $K_m$ values. By comparison with wild-type, the K47E mutant did not show a difference in binding to these four drugs, which might be related to its position being relatively far from Arg50. Based on the above results and structural information of the Arg50 loop, the basis for reduced AG337 and FdUMP binding with D49S and G52S mutants may result from impaired movement of the Arg50 loop, especially for the Arg50 residue which is involved in folate and dUMP binding. More marked changes by some mutations such as R50C, D49N and T51A result in inactive TS enzymes, while small structural perturbation of Arg50 loop due to these mutations may compensated for by the local adjustment of neighbor residues, which still maintain contacts with ligands in the new position.

Ile108 Mutants and the Role of Ile108

The human TS active site is comprised of a hydrophobic region that includes Trp109, Asn112, Met311, Ile108, Leu221 and Phe225. Multiple substitutions on positions 108, 221 and 225 were performed by site-directed mutagenesis, because these changes could alter the conformation of the TS active site and or the electrostatic environment, resulting in altered binding affinities with substrate and inhibitors leading to drug resistance.

Although Ile108 is a highly conserved amino acid residue, it shows flexibility of its side chain when antifolates occupy the folate binding site. When human TS lipophilic inhibitors such as AG337 were designed by molecular modeling, it was predicted that the side chain of Ile108 would move toward the distal phenyl ring of AG337 to make the desired non-polar interaction, resulting in the calculated minimum-energy conformation. This movement and modeled interaction were subsequently observed in the crystal structure of TS complexed to AG337. The shift of the Ile108 side chain upon AG337 binding suggested that the spatial relationship of Ile108 to bound folate and inhibitors such as AG337 is little different due to the changed molecular structure of inhibitor. Some mutations on position 108 may affect the binding of cofactor and inhibitors (AG337, tomudex and BW1843U89) that can occupy the cofactor binding site. The first two mutations made were Phe and Ala substitutions. Because of smaller side chain of alanine than isoleucine, the movement of side chain of Ala may not be enough to contact the phenyl ring of AG337. Loss or weakening of these interactions in the variants must also reduce the binding energy, resulting in dramatic changes of affinity of AG337 to TS. For phenylalanine, a non-polar amino acid, containing a phenyl group that has less flexibility, it was expected that if the stacking of phenyl-phenyl rings between inhibitor and altered human TS is impeded, TS will adopt a new conformation by reorientation of amino acid residues, thus causing a large change in enzyme behavior.

The results of cytotoxicity assays were that Ile108 replacement by residues with a smaller side chain (Ala) weakened binding of AG337 and tomudex, with respective $IC_{50}$ values at least 78- and 43-fold greater than value obtained by wild-type human TS. In contrast, the increase of the $IC_{50}$ value of BW1843U89 was relatively less (6-fold), which may reflect that the large molecular structure of BW1843U89 retains contact with the side chain of alanine. Moreover, since Ile108 is not one of residues of the substrate binding pocket, I108A mutants did not affect the FdUrd binding much with only a 12-fold increase in the $IC_{50}$ value.

In contrast, little effects on catalysis and inhibitor binding were observed for the I108F mutant. This variant behaved as same as wild-type TS, suggesting that the side hydrophobic chain substitution did not change the spatial interaction between enzyme, cofactor or inhibitors. In order to further study the role of Ile108 on cofactor and antifolate binding, this residue was replaced by Asn (a polar a.a.), Glu (an acidic a. a.) and Gly (a non-polar a.a. without a side chain). None of these three mutant enzymes could complement mouse TS-deficient cells in the absence of thymidine, showing those changes greatly decreased the catalytic efficiency due to the loss of hydrophobic contacts.

These mutagenesis studies showed that Ile108 could tolerate substitutions with hydrophobic residues (Phe and Ala) but not Gly, Asn and Glu. Moreover, the drastic differences in folate binding and catalytic activity among these variants indicate that position 108 is quite sensitive to mutagenesis and plays a critical role in folate binding. These results strongly suggest that the I108A mutation was responsible for the altered properties of human TS and was sufficient to confer significant AG337 and tomudex resistance, because it showed distinctive effects on binding affinity among three antifolates and different properties on catalysis compared to the other four mutants.

Some decrease in catalytic efficiency due to reduced affinity of substrate and cofactor binding was also observed with the I108A mutant. However, I108A was able to allow mouse TS-negative cells to grow in the absence of thymidine and to result in resistance to tomudex and AG337. In addition, transfection of mouse marrow cells with the I108A mutant cDNA resulted in more tomudex-resistant colony survival for the I108A mutant expressed cells as compared to mouse marrow cells transfected with wild-type human TS, indicating I108A mutant is a good candidate for gene transfer studies to protect bone marrow from tomudex or AG337 toxicity.

Phe225 Mutants and the Role of Phe225

Phe225 was targeted for site-directed mutagenesis, because based on the crystal structure of TS, this position contributes the major hydrophobic force on binding of the PABA moiety of $CH_2H_4$folate, and exhibited a large shift upon ternary complex formation. For accommodating different ligands, Phe225 underwent dramatic side chain movement. For example, the orientation of the phenyl group of Phe225 toward CB3717 and $H_2$folate is changed on binding to these ligands. The aromatic ring of Phe225 stacks against the propargyl group of CB3717, which could be important for the stability of CB3717 binding to TS. However, the Phe225 side chain moves away when $H_2$folate instead of CB3717 binds causing more weak and expansive van der Waals contacts, which may allow $H_2$folate to dissociate from TS. These observations indicate that when TS forms a complex with $CH_2H_4$folate, $H_2$folate, CB3717, tomudex or AG337, which all have a pterin or quinazoline ring, the mobile phenyl group of Phe225 has enough space to accommodate these ligands by different hydrophobic interactions and it is not necessary to form aromatic-aromatic non-polar interaction by face-to-face interactions between Phe225 and the folate molecule. BW1843U89 binds differently, as a consequence of an expanded benzoquinaline ring, and results in reorientation of the Phe225 phenyl ring (turn 90°) to form an aromatic π stacking with the isoindolinyl ring of BW1843U89.

The interactions of Phe225 with cofactor and various antifolates appear to be quite different. Phe225 was therefore replaced by tryptophan, tyrosine, leucine or serine. The results of transfection of mouse TS-negative cells demonstrated that this highly conserved residue could be substituted by Trp, Leu and Tyr but not by Ser. Also, the F225S and F225L mutant enzymes did not show drastic changes in binding of three antifolates (AG337, tomudex, BW1843U89) and FdUrd. In contrast, the F225W variant conferred resistance to BW1843U89 and FdUrd, with increased $IC_{50}$ values of 22- and 25-fold respectively. But, it did not lead to cross-resistance to AG337 and tomudex.

The above results indicated that the replacement of Phe225 with tryptophan, tyrosine, leucine or serine had very different effects on enzyme activity and binding affinity of inhibitors. The F225S mutant exhibited severely diminished TS catalytic activity, presumably because the hydroxyl side chain of serine decreased the hydrophobic interaction between TS and the PABA moiety of folate. Substitutions with tyrosine, a aromatic amino acid also containing a hydroxyl moiety, retained TS function. The aromatic group of Tyr may contribute hydrophobic contacts to folate compounds, along with negative binding factors caused by the hydroxyl polar group. The F225W mutant but not the F225L mutant conferred resistance to BW1843U89. The loss of the hydrophobic interaction (aromatic π stacking) between the tryptophan side chain and the isoindolinyl ring of BW1843U89 may account for the lost of binding energy for BW1843U89.

Mutations of Position 221

In the crystal structure of the human TS, Leu221, an almost invariant residue in all reported TS sequences, was a residue involved in hydrophobic contacts with bound cofactor or inhibitors. Five point mutations (phenylalanine, leucine, isoleucine, serine or arginine) were introduced at position 221 of the human TS via site-directed mutagenesis in order to evaluate whether these mutations would change the ligand binding properties of the enzyme.

Mouse TS-negative cells were rescued by transfection with Ala, Ile and Ser variants but not Phe and Arg variants. The presence of an Arg, a positive charged residue, substitution for Leu221 causing TS function loss, is explained by the loss of hydrophobic interactions. For phenylalanine substitution, a hydrophobic amino acid, because of its bulk (Phe, 142 Å$^3$ and Leu, 107 Å$^3$), may result in the L221F variant being inactive. However, when the volume of non-polar side chain was unchanged (for Ile substitution) or became smaller (for Ala) and an hydroxyl group added (for Ser), these mutations did not cause a large change in enzyme behavior. The L221A, L221I and L221S variants of human TS also did not show big differences on inhibitor binding affinities. It may suggest that the steric position of Leu221, unlike Phe225 and Ile108, is hardly moved or reoriented when cofactor or inhibitors having different molecular structures bind to enzyme.

Random Mutagenesis

Random mutagenesis by EMS exposure and following AG337 selection resulted in the generation of a large number of resistant clones. Without EMS pretreatment, only 1 (1/10$^8$ vs 4¼×10$^8$) clone survived the selecting dose of AG337. Fourty one of these clones were expanded to obtain stable AG337-resistant cell lines. DNA-SSCP analysis suggested that 9 of 41 AG337-resistant cell lines with altered mobility on SSCP gels may have acquired mutations in the TS gene. Analysis of these 9 AG337-resistant sublines by whole cell in situ TS assay as well as Northern and Western blotting revealed that some resistant sublines demonstrated elevation of TS mRNA and enzyme levels, and cross-resistance to other TS-directed drugs tomudex and FdUrd, but some sublines did not overexpress TS mRNA and protein. Twenty mutations in TS in AG337-resistant cell lines were identified, resulting in gene amplification as well as mutations in the coding region. Of 8 mutations chosen for rescue studies of mouse TS-negative cells, three TS mutants (K47E, D49G and G52S) were able to allow growth of TS-negative cells in the absence of thymidine, indicating they retain TS catalytic activity. D49S or G52S transfected in mouse TS-negative cells confer resistance to AG337 with $IC_{50}$ values 40- and 12-fold greater than wild-type TS transfected cells respectively. They also display resistance to FdUrd (respective 26- and 97-fold) but not to tomudex or BW1843U89. The structural perturbation of the Arg50 loop due to D49S or G52S mutations may cause resistance to AG337 and FdUrd. The $K_m$ for $CH_2H_4$folate and dUMP of the D49G variant was increased 4-fold over wild-type TS.

Site-Directed Mutagenesis

Three amino acids, determined to be important for hydrophobic interactions between the folate cofactor (inhibitors) and human TS, were chosen for site-directed mutagenesis studies. Ile108 was mutated to Ala, Phe, Gly, Glu and Asn. Only I108A and I108F TS mutants were functional. I108A mutant transfected cells confer resistance to tomudex and AG337 with respective $IC_{50}$ values at least 43- and 78-fold greater than wild-type TS transfected cells but not to BW1843U89 and FdUrd. The I108A mutant also was found to have a decrease in $k_{cat}$ and an increase in $K_m$ ($CH_2H_4$folate). The changes in the side chain due to I108A mutation may cause the loss of hydrophobic interactions between position 108 and the phenyl ring of AG337 and tomudex, resulting in reduced binding affinity of these molecules. Secondly, Phe225 was replaced by Trp, Ser, Leu and Tyr. F225W, F225L and F225Y are active enzymes. The F225W mutant displayed resistance to BW1843U89 without changes in $V_{max}$ and $K_m$ (dUMP). The perturbation of the aromatic π stacking between the tryptophan side chain and the isoindolinyl ring of BW1843U89 may account for the lost binding energy for BW1843U89 to TS. Thirdly, L221A, L221I, L221S, L221F and L221R mutants were created by site-directed mutagenesis. TS catalytic activity could be restored by Ala, Ile and Ser but not Phe and Arg mutants. Fourthly, I108A (for tomudex and AG337), G52S (for 5-FU) and F225W (for BW1843U89) human TS mutants are representative examples of mutants for gene transfer studies.

The present invention isolated and characterized human TS mutants conferring antifolates or 5-PU resistance. Based on the presented findings, there are two major applications including resistant gene transfer studies and crystal structure analysis of TS variants. For example, resistance to 5-FU has been related to insufficient inhibition of tumor TS. Higher 5-FU doses may increase the success of chemotherapy of certain cancer. The transduction of hematopoietic precursor cells with the G52S mutant TS cDNA would allow dose-intense therapy of 5-FU in cancer patient by decreasing myelotoxicity. Another important application is X-ray crystallographic studies of three mutants (G52S, I108A and F225W). The three-dimensional structural data would provide information of how the mutated residues participate in inhibitor binding or how the altered residues interfere with inhibitor binding through steric hindrance (for F225W), the loss of hydrophobic interaction (for I108A) or structural perturbation (for G52S). The knowledge of the difference of wild-type and mutant human TS structures may also be of value in the design of new TS inhibitors with desirable properties.

The following tables 15–17 summarize additional proof that these mutants confer resistance to chemotherapeutic agents by increasing the number of drug resistant CFU-GM colonies formed by murine bone marrow cells infected with retroviral vectors containing these mutant TS cDNAs.

TABLE 15

Colony Forming Unit-Granulocyte Macrophage (CFU-GM) assay incubated with 5-FluoroUracil for 10 days

| | No drug | | $10^{-5}$ M 5-FU | $10^{-6}$ M 5-FU | |
|---|---|---|---|---|---|
| | CFU-C* | HPPCFU-C** | CFU-C | CFU-C | HPPCFU-C |
| Normal Bone Marrow | 160 | 40 | 0 | 16(10%) | 0 |
| Wt TS | 168 | 44 | 0 | 91(54%) | 6(14%) |
| G52S mut-TS | 162 | 53 | 10(6%) | 117(72%) | 21(40%) |

*CFU-C: colony forming units;
**HPPCFU-C: high proliferative potential CFU-C

TABLE 16 incubated with Tomudex $^R$ (D-1694)

| | No drug | | $2 \times 10^{-8}$ M | $1 \times 10^{-8}$ M | |
|---|---|---|---|---|---|
| | CFU-C* | HPPCFU-C** | CFU-C | CFU-C | HPPCFU-C |
| Normal Bone Marrow | 160 | 40 | 0 | 16(10%) | 0 |
| Wt TS | 168 | 44 | 10(6%) | 33(20%) | 10(23%) |
| I108A mut-TS | 148 | 49 | 25(15%) | 53(36%) | 26(53%) |

*CFU-C: colony forming units;
**HPPCFU-C: high proliferative potential CFU-C

TABLE 17

| | incubated with AG337 (Thymitaq) | | | | |
|---|---|---|---|---|---|
| | No drug | | $5 \times 10^{-7}$ M | $1 \times 10^{-7}$ M | |
| | CFU-C* | HPPCFU-C** | CFU-C | CFU-C | HPPCFU-C |
| Normal Bone Marrow | 160 | 40 | 0 | 16(10%) | 0 |
| Wt TS | 168 | 44 | 0 | 71(42%) | 13(30%) |
| I108A mut-TS | 148 | 49 | 9(6%) | 110(36%) | 38(78%) |

*CFU-C: colony forming units;
**HPPCFU-C: high proliferative potential CFU-C

The following references were cited herein:
Appelt, et al., (1991) *J. Med. Chem.* 34(7):1925–1934.
Ayusawa, et al., (1981) *Somatic. Cell Genet.* 7(5):523–534.
Barbour, et al., (1990) *Mol. Phurmacol.* 37:515–518.
Barbour, et al., (1992) *Mol. Pharmacol.* 42:242–248.
Belfort, et al., (1983a) *J. Biol. Chem.* 258:2045–2051.
Belfort, et al., (1983b) *Proc. Natl. Acad. Sci. USA* 80:4914–4918.
Brail, et al., (1993) *Mutation Res.* 303:171–175.
Carreras, et al., (1992) *Biochemistry* 31(26):6038–6044.
Carreras, et al., (1995) *Annu. Rev. Biochem.* 64:721–62.
Cassidy, et al., (1994) *Hematology-Oncology Clinics of North America* 8(2):289–303.
Chu, et al., (1991) *Proc. Natl. Acad. Sci. USA* 88:8977–8981.
Chu, et al., (1993) *Proc. Natl. Acad. Sci. USA* 90:517–521.
Ciasla, et al., (1995) *Biochim. Biophys. Acta* 1261:233–242.
Cisneros, et al., (1990) *Anal. Biochem.* 186:202–208.
Climie, et al., (1990a) *Proc. Natl. Acad. Sci. USA* 87:633–637.
Climie, et al., (1990b) *J. Biol. Chem.* 265(31):18776–18779.
Climie, et al., (1992) *Biochemistry* 31:6032–6038.
Danenberg, et al., (1979) *J. Biol. Chem.* 254(11):4345–4348.
Danenberg, et al., (1981) *Pharmacol. Ther.* 13:69–90.
Davisson, et al., (1989) *J. Biol. Chem.* 264(16):9145–9148.
Davisson, et al., (1994) *J. Biol. Chem.* 269:30740.
Dev, et al., (1988) *Proc. Natl. Acad. Sci. USA* 85:1472–1476.
Dev, (1994) *J. Biol. Chem.* 269(3):1873–1882.
Drake, (1996) *Biochem. Pharmacol.* 51:1349–1355.
Eckstein, et al., (1994) *Biochemistry* 33:15086–15094.
Fanin, et al., (1993) *Mol. Pharmacol.* 44:13–21.
Fauman, et al., (1994) *Biochemistry* 33:1502–1511.
Fernandes, et al., (1985) *Biochem. Pharmacol.* 34:125–132.
Finer-Moore, et al., (1993) *J. Mol. Biol.* 232:1101–1116.
Finer-Moore, et al., (1994) *Biochemistry* 33:15459–15468.
Fleming, et al., (1992) *Seminars in Oncol.* 19(6):707–719.
Grem, et al., (1986) *Cancer Res.* 46:6191–6199.
Gibson, et al., (1993) *Biochem. Pharmacol.* 45(4):863–869.
Grumont, et al., (1988) *Biochemistry* 27:3776–3784.
Hardy, et al., (1987) *Science* 235:448–455.
Hardy, et al., (1992) *Pro. Natl. Acad. Sci, USA* 89:9725–9729.
Herrmann, R. (1995) *Eur. J. Cancer* 31A(12):1919–1920.
Hongyo, et al., (1993) *Nucleic Acids Res.* 21(16):3637–3642.
Hughey, et al., (1993) *Mol. Pharmacol.* 44:316–323.
Jackman, et al., (1991a) *Cancer Res.* 51:5579–5586.
Jackman, et al., (1991b) *Adv. Exp. Med. Biol.* 309A:19–23.
Jackman, et al., (1991c) *Adv. Enzyme Reg.* 31:13–27.
Jackman, et al., (1993) *Adv. Exp. Med. Biol.* 339:265–276.
Jackman, et al., (1995a) *Br. J. Cancer* 71:914–924.
Jackman, et al., (1995b) *Annals of Oncology* 6:971–881.
Jodrell, et al., (1991). *Br. J. Cancer* 64:833–838.
Jones, et al., (1981) *Eur. J. Cancer* 17:11–19.
Kamb, et al., (1992a) *Biochemistry* 31(41):9883–9890.
Kamb, et al., (1992b) *Biochemistry* 31:12876–12884.
Keyomarsi, et al., (1990) *J. Biol. Chem.* 265(31):19163–19169.
Keyomarsi, et al., (1993) *J. Biol. Chem.* 268(20):15412–15149.
Kim, et al., (1992) *Proteins* 13:352–363.
Knight, et al., (1989) *Advan. Enzyme Regul.* 29:3–12.
Knighton, et al., (1994) *Nat. Struct. Biol.* 1(3):186–194.
Koc, et al., (1996) *Seminars in Oncology* 23(1):46–65.
LaPat-Polasko, et al., (1990) *Biochemistry* 29:9561–9572.
Liu, L., Santi, D. V. (1992) *Biochemistry* 31(22):5100–5104.
Liu, L., Santi, D. V. (1993) *Biochemistry* 32(36):9263–9267.
Lu, et al., (1995) *Biochem. Pharmacol.* 50(3):391–398.
Maley, et al., (1979) *J. Biol. Chem.* 254:1301–1304.
Maley, F. and Maley, G. F. (1990) *Prog. Nucleic Acid Res. Mol. Biol.* 39:49–80.
Matthews, et al., (1990a) *J. Mol. Biol.* 214:923–936.
Matthews, et al., (1990b) *J. Mol. Biol.* 214:937–948.
Michaels, et al., (1990) *Proc. Natl. Acad. Sci. USA* 87:3957–3961.
Montfort, et al., (1990) *Biochemistry* 29:6964–6977.
Moore, et al., *Protein Expression and purification* 4:60–163.
Mulkins, M. A., and Heidelberger, C. (1982) *Cancer Res.* 42:965–973.
Nord, L. D., and Martin, D. S. (1993) *Current Opinion in Oncology* 5:1017–1022.
Perry, et al., (1990) *Proteins.* 8:315–333.
Perston, B. D. and Doshi, R. (1990). Molecular targets of chemical mutagens. *Biological Reactive Intermediates IV*, Edited by C. M. Witmer et al. Plenum Press, New York.
Pinedo, H. M. and Peters, G. F. (1988) *J. Clin. Oncol.* 6(10):16535–1664.
Pogolotti, et al., (1986) *J. Med. Chem.* 29:478–482.
Reich, et al., (1992) *J. Med. Chem.* 35(5):847–858.
Rode, et al., (1979) *J. Biol. Chem.* 254(22):11538–11543.
Santi, et al., (1990) *J. Biol. Chem.* 265(12):6770–6775.
Santi, D. V. and Danenberg, P. V. (1984). Folates in pyrimidine nucleotide biosynthesis. *Folates and Pterins, vol. 1: Chemistry and Biochemistry of Folates* (Blakley, R. L., & Benkovic, S. J., Eds.), John Wiley and Sons, New York, 345–398.
Schiffer, et al., (1991) *J. Mol. Biol.* 219:161–163.
Schiffer, et al., (1995) *Biochemistry* 34:16279–16287.
Schweitzer, et al., (1989) *J. Biol. Chem.* 264:20786–20795.
Sega, G. A. (1984) *Mutation Res.* 134:113–142.
Sheffield, et al., (1993) *Genomics* 16:325–332.
Shoichet, et al., (1993) *Science* 259(5):1445–1450.
Simonstian, et al., (1983) *Proc. Natl. Acad. Sci. USA* 80:2495–2499.
Sobrero, et al., (1985) *Cancer Res.* 45:3155–3160.
Stout, T. J. and Stroud, R. M. (1996) *Structure* 4(1):67–77.
Stroud, R. M. and Finer-Moore, J. S. (1993) *FASEB J.* 7:671–677.

Takeishi, et al., (1985) *Nucleic Acids Res.* 13(6):2035–2043.
Tindall, et al., (1988) *Biochemistry* 27(16):6008–6013.
Touroutoglou, N., and Pazdue, R. (1996). Thymidylate synthase inhibitors. *Clinical Cancer Research* 2:227–243.
Varney, et al., (1992) *J. Med. Chem.* 35:663–676.
Wahba, A. J. and Friedkin, M. (1961) *J. Biol. Chem.* 236:PC11–12.
Webber, et al., (1993) *J. Med. Chem.* 36:733–746.
Webber, et al., (1996) *Cancer Chemotherapy & Pharmacology* 37(6):509–17.
Weichsel, et al., (1995) *Proc. Natl. Acad. Sci. USA* 92:3493–3497.
Wells, et al., (1985) *Gene* 34:315–323.
Zhang, et al., (1989) *Gene* 84:487–491.
Zhang, et al., (1990) *Biochem. Biophys. Res. Commun.* 167(3):869–875.
Zhang, et al., (1992) *Seminars in Oncology.* 19(2):4–9.
Zhao, et al., (1995) *Proceedings of the American Association for Cancer Research.* 36:502(Abstract 2989).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A mutated human thymidylate synthase (TS), said mutated synthase differing from wild type TS having the amino acid sequence of SEQ ID No. 39 at amino acid residue 49, amino acid residue 52, amino acid residue 108, amino acid residue 221 or amino acid residue 225.

2. The mutated human TS of claim 1, wherein said amino acid residue 49 is mutated to an amino acid selected from the group consisting of glycine and asparagine.

3. The mutated human TS of claim 1, wherein said amino acid residue 52 is mutated to serine.

4. The mutated human TS of claim 1, wherein said amino acid residue 108 is mutated to an amino acid selected from the group consisting of alanine, phenylalanine, glycine, glutamic acid and asparagine.

5. The mutated human TS of claim 1, wherein said amino acid residue 221 is mutated to an amino acid selected from the group consisting of phenylalanine, arginine, alanine, isoleucine and serine.

6. The mutated human TS of claim 1, wherein said amino acid residue 225 is mutated to an amino acid selected from the group consisting of tryptophan, serine, leucine and tyrosine.

7. A cDNA derived from a wild type cDNA, said wild type cDNA having the nucleotide sequence of SEQ ID No. 38, wherein said derived cDNA has been mutated to encode the mutated human TS of claim 1.

8. A DNA vector, said vector comprising:

DNA derived from a wild type cDNA, said wild type cDNA having the nucleotide sequence of SEQ ID No. 38, wherein said DNA has been mutated to encode the mutated human TS of claim 1.

9. A host cell, said host cell transfected with the DNA vector of claim 8, wherein said host cell produces the mutated human TS of claim 1.

10. The host cell of claim 9, wherein said cell is a mammalian hematopoietic cell.

11. The host cell of claim 10, wherein said cell is a peripheral blood stem cell.

* * * * *

UNITED STATES PATENT AND TRADEMARK OFFICE
CERTIFICATE OF CORRECTION

PATENT NO. : 6,416,987 B1
APPLICATION NO. : 09/367007
DATED : July 9, 2002
INVENTOR(S) : Liu-Chen et al.

It is certified that error appears in the above-identified patent and that said Letters Patent is hereby corrected as shown below:

Insert after line 5 of Column 1, the following:

--Federal Funding Legand

This invention was created, in part, using funds from the federal government under National Institutes of Health Grant No. CA08010. Consequently, the U.S. government has certain rights in this invention.--

Signed and Sealed this

Fifteenth Day of January, 2008

JON W. DUDAS
*Director of the United States Patent and Trademark Office*

SEQUENCE LISTING

```
<160> NUMBER OF SEQ ID NOS: 39

<210> SEQ ID NO 1
<211> LENGTH: 15
<212> TYPE: DNA
<213> ORGANISM: artificial sequence
<220> FEATURE:
<223> OTHER INFORMATION: Nucleotide sequence in the 5' coding region of
      human recombinants cDNA of thymidylate synthase
      (TS) gene in pET-17(bhTS) vector.

<400> SEQUENCE: 1
atgcctgtgg ccggc                                                   15

<210> SEQ ID NO 2
<211> LENGTH: 15
<212> TYPE: DNA
<213> ORGANISM: artificial sequence
<220> FEATURE:
<223> OTHER INFORMATION: Altered nucleotide sequence in the 5' coding
      region of human recombinants cDNA of thymidylate synthase (TS)
      gene in pET-17(bhTS) vector.

<400> SEQUENCE: 2
atgcttgttg ctggt                                                   15

<210> SEQ ID NO 3
<211> LENGTH: 20
<212> TYPE: DNA
<213> ORGANISM: artificial sequence
<220> FEATURE:
<221> NAME/KEY: primer_bind
<222> LOCATION: 50..69
<223> OTHER INFORMATION: Sense primer hTS-1A for PCR amplification of
      part of 890 base pair fragment of human TS gene from nucleotide
      50 to the C-terminus

<400> SEQUENCE: 3
cacaggagcg ggacgccgag                                              20

<210> SEQ ID NO 4
<211> LENGTH: 21
<212> TYPE: DNA
<213> ORGANISM: artificial sequence
<220> FEATURE:
```

```
<221> NAME/KEY: primer_bind
<222> LOCATION: 354..334
<223> OTHER INFORMATION: Antisense primer hTS-1B for PCR amplification
      of part of 890 base pair fragment of human TS gene from nucleotide
      50 to the C-terminus

<400> SEQUENCE: 4
caaaaagtct cgggatccat t                                             21

<210> SEQ ID NO 5
<211> LENGTH: 22
<212> TYPE: DNA
<213> ORGANISM: artificial sequence
<220> FEATURE:
<221> NAME/KEY: primer_bind
<222> LOCATION: 298..319
<223> OTHER INFORMATION: Sense primer hTS-2A for PCR amplification of
      part of 890 base pair fragment of human TS gene from nucleotide
      50 to the C-terminus

<400> SEQUENCE: 5
gagctgtctt ccaagggagt ga                                            22

<210> SEQ ID NO 6
<211> LENGTH: 24
<212> TYPE: DNA
<213> ORGANISM: artificial sequence
<220> FEATURE:
<221> NAME/KEY: primer_bind
<222> LOCATION: 645..622
<223> OTHER INFORMATION: Antisense primer hTS-2B for PCR amplification
      of part of 890 base pair fragment of human TS gene from nucleotide
      50 to the C-terminus

<400> SEQUENCE: 6
tctctggtac agctggcagg acag                                          24

<210> SEQ ID NO 7
<211> LENGTH: 26
<212> TYPE: DNA
<213> ORGANISM: artificial sequence
<220> FEATURE:
<221> NAME/KEY: primer_bind
<222> LOCATION: 594..616
<223> OTHER INFORMATION: Sense primer hTS-3A for PCR amplification of
      part of 890 base pair fragment of human TS gene from nucleotide
      50 to the C-terminus

<400> SEQUENCE: 7
ctgccagttc tatgtggtga acagtg                                        26

<210> SEQ ID NO 8
<211> LENGTH: 24
<212> TYPE: DNA
<213> ORGANISM: artificial sequence
<220> FEATURE:
<221> NAME/KEY: primer_bind
<222> LOCATION: 939..915
<223> OTHER INFORMATION: Antisense primer hTS-3B for PCR amplification
      of part of 890 base pair fragment of human TS gene from nucleotide
      50 to the C-terminus

<400> SEQUENCE: 8
aacagccatt tccattttaa tagt                                          24

<210> SEQ ID NO 9
<211> LENGTH: 21
<212> TYPE: DNA
<213> ORGANISM: artificial sequence
```

```
<220> FEATURE:
<221> NAME/KEY: primer_bind
<222> LOCATION: 97..117
<223> OTHER INFORMATION: Sense primer hTS-4A for PCR amplification of
      part of 890 base pair fragment of human TS gene from nucleotide
      50 to the C-terminus

<400> SEQUENCE: 9
tacctggggc agatccaaca c                                              21

<210> SEQ ID NO 10
<211> LENGTH: 23
<212> TYPE: DNA
<213> ORGANISM: artificial sequence
<220> FEATURE:
<221> NAME/KEY: primer_bind
<222> LOCATION: 210..188
<223> OTHER INFORMATION: Antisense primer hTS-4B for PCR amplification
      of part of 890 base pair fragment of human TS gene from nucleotide
      50 to the C-terminus

<400> SEQUENCE: 10
ttcatctctc aggctgtagc gcg                                            23

<210> SEQ ID NO 11
<211> LENGTH: 25
<212> TYPE: DNA
<213> ORGANISM: artificial sequence
<220> FEATURE:
<221> NAME/KEY: primer_bind
<222> LOCATION: 451..475
<223> OTHER INFORMATION: Sense primer hTS-5A for PCR amplification of
      part of 890 base pair fragment of human TS gene from nucleotide
      50 to the C-terminus

<400> SEQUENCE: 11
tcagattatt caggacaggg agttg                                          25

<210> SEQ ID NO 12
<211> LENGTH: 23
<212> TYPE: DNA
<213> ORGANISM: artificial sequence
<220> FEATURE:
<221> NAME/KEY: primer_bind
<222> LOCATION: 503..481
<223> OTHER INFORMATION: Antisense primer hTS-5B for PCR amplification
      of part of 890 base pair fragment of human TS gene from nucleotide
      50 to the C-terminus

<400> SEQUENCE: 12
atggtgtcaa tcactctttg cag                                            23

<210> SEQ ID NO 13
<211> LENGTH: 24
<212> TYPE: DNA
<213> ORGANISM: artificial sequence
<220> FEATURE:
<221> NAME/KEY: primer_bind
<222> LOCATION: 756..779
<223> OTHER INFORMATION: Sense primer hTS-6A for PCR amplification of
      part of 890 base pair fragment of human TS gene from nucleotide
      50 to the C-terminus

<400> SEQUENCE: 13
gggagatgca catatttacc tgaa                                           24

<210> SEQ ID NO 14
<211> LENGTH: 20
<212> TYPE: DNA
```

```
<213> ORGANISM: artificial sequence
<220> FEATURE:
<221> NAME/KEY: primer_bind
<222> LOCATION: 822..803
<223> OTHER INFORMATION: Antisense primer hTS-6B for PCR amplification
      of part of 890 base pair fragment of human TS gene from nucleotide
      50 to the C-terminus

<400> SEQUENCE: 14
tctgggttct cgctgaagct                                              20

<210> SEQ ID NO 15
<211> LENGTH: 24
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Phe225 to Trp225 point mutation in hTS

<400> SEQUENCE: 15
cggtgtgcct tggaacatcg ccag                                         24

<210> SEQ ID NO 16
<211> LENGTH: 24
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Phe225 to Ser225 point mutation in hTS

<400> SEQUENCE: 16
cggtgtgcct tccaacatcg ccag                                         24

<210> SEQ ID NO 17
<211> LENGTH: 24
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Phe225 to Leu225 point mutation in hTS

<400> SEQUENCE: 17
ctcggtgtgc ctctcaacat cgcc                                         24

<210> SEQ ID NO 18
<211> LENGTH: 24
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Phe225 to Tyr225 point mutation in hTS

<400> SEQUENCE: 18
cggtgtgcct tacaacatcg ccag                                         24

<210> SEQ ID NO 19
<211> LENGTH: 25
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Leu221 to Phe221 point mutation in hTS

<400> SEQUENCE: 19
```

```
ggagacatgg gcttcggtgt gcctt                                           25

<210> SEQ ID NO 20
<211> LENGTH: 26
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Leu221 to Arg221 point mutation in hTS

<400> SEQUENCE: 20
gagacatggg ccgcggtgtg cctttc                                          26

<210> SEQ ID NO 21
<211> LENGTH: 24
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Leu221 to Ala221 point mutation in hTS

<400> SEQUENCE: 21
gagacatggg cgccggtgtg cctt                                            24

<210> SEQ ID NO 22
<211> LENGTH: 22
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Leu221 to Ile221 point mutation in hTS

<400> SEQUENCE: 22
gagacatggg catcggtgtg cc                                              22

<210> SEQ ID NO 23
<211> LENGTH: 24
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Leu221 to Ser221 point mutation in hTS

<400> SEQUENCE: 23
gagacatggg cagcggtgtg cctt                                            24

<210> SEQ ID NO 24
<211> LENGTH: 22
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Ile108 to Ala108 point mutation in hTS

<400> SEQUENCE: 24
gggagtgaaa gcctgggatg cc                                              22

<210> SEQ ID NO 25
<211> LENGTH: 26
<212> TYPE: DNA
<213> ORGANISM: artificial sequence
<220> FEATURE:
```

```
<221> NAME/KEY: primer_bind
<223> OTHER INFORMATION: Mutagenic oligonucleotide sequence used to
      obtain Ile108 to Phe108 point mutation in hTS

<400> SEQUENCE: 25
caagggagtg aaattctggg atgcca                                    26

<210> SEQ ID NO 26
<211> LENGTH: 22
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Ile108 to Gly108 point mutation in hTS

<400> SEQUENCE: 26
gggagtgaaa ggctgggatg cc                                        22

<210> SEQ ID NO 27
<211> LENGTH: 22
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Ile108 to Glu108 point mutation in hTS

<400> SEQUENCE: 27
gggagtgaaa gagtgggatg cc                                        22

<210> SEQ ID NO 28
<211> LENGTH: 22
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Ile108 to Asn108 point mutation in hTS

<400> SEQUENCE: 28
gggagtgaaa aactgggatg cc                                        22

<210> SEQ ID NO 29
<211> LENGTH: 25
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Asp49 to Asn49 point mutation in hTS

<400> SEQUENCE: 29
gtcaggaagg acaaccgcac gggca                                     25

<210> SEQ ID NO 30
<211> LENGTH: 25
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Asp49 to Gly49 point mutation in hTS

<400> SEQUENCE: 30
tcaggaagga cggccgcacg ggcac                                     25
```

```
<210> SEQ ID NO 31
<211> LENGTH: 25
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Thr51 to Ala51 point mutation in hTS

<400> SEQUENCE: 31
aaggacgacc gcgcgggcac cggca                                    25

<210> SEQ ID NO 32
<211> LENGTH: 23
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Lys47 to Glu47 point mutation in hTS

<400> SEQUENCE: 32
gcggcgtcag ggaggacgac cgc                                      23

<210> SEQ ID NO 33
<211> LENGTH: 25
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Arg50 to Cys50 point mutation in hTS

<400> SEQUENCE: 33
aggaaggacg actgcacggg caccg                                    25

<210> SEQ ID NO 34
<211> LENGTH: 26
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Gly52 to Ser52 point mutation in hTS

<400> SEQUENCE: 34
gacgaccgca cgagcaccgg caccct                                   26

<210> SEQ ID NO 35
<211> LENGTH: 25
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Phe59 to Leu59 point mutation in hTS

<400> SEQUENCE: 35
accctgtcgg tactcggcat gcagg                                    25

<210> SEQ ID NO 36
<211> LENGTH: 26
<212> TYPE: DNA
<213> ORGANISM: artificial sequence
<220> FEATURE:
<221> NAME/KEY: primer_bind
<223> OTHER INFORMATION: Mutagenic oligonucleotide sequence used to
      obtain Gln214 to Arg214 point mutation in hTS
```

<400> SEQUENCE: 36
tgccagctgt accggagatc gggaga                                26

<210> SEQ ID NO 37
<211> LENGTH: 25
<212> TYPE: DNA
<213> ORGANISM: artificial sequence
<220> FEATURE:
<221> NAME/KEY: primer_bind
<223> OTHER INFORMATION: Selection primer for destroying the unique SmaI
      restriction site to generate another unique KspI site on
      pcDNA3vector

<400> SEQUENCE: 37
caaaaagctc cgcggagctt gtata                                 25

<210> SEQ ID NO 38
<211> LENGTH: 1536
<212> TYPE: DNA
<213> ORGANISM: Homo sapiens
<220> FEATURE:
<223> OTHER INFORMATION: Wild type human thymidylate synthase cDNA
      (Genbank Accession number IM 001071)

<400> SEQUENCE: 38
gggggggggg ggaccacttg gcctgcctcc gtcccgccgc gccacttggc ctgcctccgt      60
cccgccgcgc cacttcgcct gcctccgtcc cccgcccgcc gcgccatgcc tgtggccggc     120
tcggagctgc cgcgccggcc cttgccccc gccgcacagg agcgggacgc cgagccgcgt     180
ccgccgcacg gggagctgca gtacctgggg cagatccaac acatcctccg ctgcggcgtc     240
aggaaggacg accgcacggg caccggcacc ctgtcggtat cggcatgca ggcgcgctac     300 agcctgagag atgaattccc tctgctgaca accaaacgtg tgttctggaa gggtgttttg     360
gaggagttgc tgtggtttat caagggatcc acaaatgcta agagctgtc ttccaaggga     420 gtgaaaatct gggatgccaa tggatcccga acttttggg acagcctggg attctccacc     480
agagaagaag gggacttggg cccagttat ggcttccagt ggaggcattt tggggcagaa     540
tacagagata tggaatcaga ttattcagga cagggagttg accaactgca agagtgatt     600 gacaccatca aaaccaaccc tgacgacaga agaatcatca tgtgcgcttg aatccaaga     660 gatcttcctc tgatggcgct gcctccatgc catgccctct gccagttcta tgtggtgaac     720
agtgagctgt cctgccagct gtaccagaga tcgggagaca tgggcctcgg tgtgcctttc     780
aacatcgcca gctacgccct gctcacgtac atgattgcgc acatcacggg cctgaagcca     840
ggtgacttta tacacacttt gggagatgca catatttacc tgaatcacat cgagccactg     900
aaaattcagc ttcagcgaga acccagacct ttcccaaagc tcaggattct cgaaaagtt     960 gagaaaattg atgacttcaa agctgaagac tttcagattg aagggtacaa tccgcatcca    1020
actattaaaa tggaaatggc tgtttagggt gctttcaaag gagcttgaag gatattgtca    1080
gtctttaggg gttgggctgg atgccgaggt aaaagttctt tttgctctaa aagaaaaagg    1140
aactaggtca aaaatctgtc cgtgacctat cagttattaa ttttttaagga tgttgccact    1200 ggcaaatgta actgtgccag ttctttccat aataaaaggc tttgagttaa ctcactgagg    1260
gtatctgaca atgctgaggt tatgaacaaa gtgaggagaa tgaaatgtat gtgctcttag    1320
caaaaacatg tatgtgcatt tcaatcccac gtacttataa agaaggttgg tgaatttcac    1380
aagctatttt tggaatattt ttagaatatt ttaagaattt cacaagctat tccctcaaat    1440
ctgagggagc tgagtaacac catcgatcat gatgtagagt gtggttatga actttatagt    1500

```
tgttttatat gttgctataa taaagaagtg ttctgc                                    1536
```

<210> SEQ ID NO 39
<211> LENGTH: 313
<212> TYPE: PRT
<213> ORGANISM: Homo sapiens
<220> FEATURE:
<223> OTHER INFORMATION: Wild type human thymidylate synthase amino acid
      sequence (Genbank Accession number NP001062)

<400> SEQUENCE: 39

```
Met Pro Val Ala Gly Ser Glu Leu Pro Arg Arg Pro Leu Pro Pro
                 5                  10                  15

Ala Ala Gln Glu Arg Asp Ala Glu Pro Arg Pro Pro His Gly Glu
             20                  25                  30

Leu Gln Tyr Leu Gly Gln Ile Gln His Ile Leu Arg Cys Gly Val
             35                  40                  45

Arg Lys Asp Asp Arg Thr Gly Thr Gly Thr Leu Ser Val Phe Gly
             50                  55                  60

Met Gln Ala Arg Tyr Ser Leu Arg Asp Glu Phe Pro Leu Leu Thr
             65                  70                  75

Thr Lys Arg Val Phe Trp Lys Gly Val Leu Glu Glu Leu Leu Trp
             80                  85                  90

Phe Ile Lys Gly Ser Thr Asn Ala Lys Glu Leu Ser Ser Lys Gly
             95                 100                 105

Val Lys Ile Trp Asp Ala Asn Gly Ser Arg Asp Phe Leu Asp Ser
            110                 115                 120

Leu Gly Phe Ser Thr Arg Glu Glu Gly Asp Leu Gly Pro Val Tyr
            125                 130                 135

Gly Phe Gln Trp Arg His Phe Gly Ala Glu Tyr Arg Asp Met Glu
            140                 145                 150

Ser Asp Tyr Ser Gly Gln Gly Val Asp Gln Leu Gln Arg Val Ile
            155                 160                 165

Asp Thr Ile Lys Thr Asn Pro Asp Asp Arg Arg Ile Ile Met Cys
            170                 175                 180

Ala Trp Asn Pro Arg Asp Leu Pro Leu Met Ala Leu Pro Pro Cys
            185                 190                 195

His Ala Leu Cys Gln Phe Tyr Val Val Asn Ser Glu Leu Ser Cys
            200                 205                 210

Gln Leu Tyr Gln Arg Ser Gly Asp Met Gly Leu Gly Val Pro Phe
            215                 220                 225

Asn Ile Ala Ser Tyr Ala Leu Leu Thr Tyr Met Ile Ala His Ile
            230                 235                 240

Thr Gly Leu Lys Pro Gly Asp Phe Ile His Thr Leu Gly Asp Ala
            245                 250                 255

His Ile Tyr Leu Asn His Ile Glu Pro Leu Lys Ile Gln Leu Gln
            260                 265                 270

Arg Glu Pro Arg Pro Phe Pro Lys Leu Arg Ile Leu Arg Lys Val
            275                 280                 285

Gly Lys Ile Asp Asp Phe Lys Ala Glu Asp Phe Gln Ile Glu Gly
            290                 295                 300

Tyr Asn Pro His Pro Thr Ile Lys Met Glu Met Ala Val
            305                 310
```